United States Patent
Wang et al.

(10) Patent No.: US 9,927,431 B2
(45) Date of Patent: Mar. 27, 2018

(54) EXTERNAL FIELD—FREE MAGNETIC BIOSENSOR

(75) Inventors: Jian-Ping Wang, Shoreview, MN (US);
Yuanpeng Li, Minneapolis, MN (US);
Wang Yi, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 792 days.

(21) Appl. No.: 14/343,252

(22) PCT Filed: Sep. 14, 2012

(86) PCT No.: PCT/US2012/055618
§ 371 (c)(1),
(2), (4) Date: Jun. 16, 2014

(87) PCT Pub. No.: WO2013/040489
PCT Pub. Date: Mar. 21, 2013

(65) Prior Publication Data
US 2015/0044778 A1    Feb. 12, 2015

Related U.S. Application Data

(60) Provisional application No. 61/534,636, filed on Sep. 14, 2011.

(51) Int. Cl.
*G01N 33/543* (2006.01)
*G01N 27/74* (2006.01)
(Continued)

(52) U.S. Cl.
CPC ..... *G01N 33/54326* (2013.01); *G01N 27/745* (2013.01); *G01R 33/0052* (2013.01);
(Continued)

(58) Field of Classification Search
CPC ........... G01N 33/54326; G01N 27/745; G01R 33/0052; G01R 33/09; G01R 33/07; G01R 33/093; G01R 33/1269
See application file for complete search history.

(56) References Cited

U.S. PATENT DOCUMENTS 6,743,639 B1   6/2004   Tondra et al.
8,076,161 B2  12/2011   Ikeda
(Continued)

FOREIGN PATENT DOCUMENTS

CN   1625686 A     6/2005
CN   101004416 A   7/2007
(Continued)

OTHER PUBLICATIONS

Abdi et al., "Surface Plasmon Resonance Sensing Detection of Mercury and Lead Ions Based on Conducting Polymer Composite," PLoS One, vol. 6, No. 9, Sep. 2011, 4 pp.
(Continued)

*Primary Examiner* — Sean E Conley
*Assistant Examiner* — Matthew D Krcha
(74) *Attorney, Agent, or Firm* — Shumaker & Sieffert, P.A.

(57) ABSTRACT

A biosensor includes a magnetic structure having grooved surface to biologically bond magnetic labels to a biological substance within the grooves. The grooves are positioned within the magnetic structure so that stray magnetic fields from the magnetic structure magnetize magnetic labels within the groove. The magnetic labels may be magnetic nanoparticles or magnetic microbeads. The techniques may reduce or eliminate the usage of any external magnetic field generator, e.g., electromagnets or current lines.

32 Claims, 19 Drawing Sheets

(51) Int. Cl.
  G01R 33/09  (2006.01)
  G01R 33/12  (2006.01)
  G01R 33/00  (2006.01)
  G01R 33/07  (2006.01)
(52) U.S. Cl.
  CPC ............. *G01R 33/07* (2013.01); *G01R 33/09* (2013.01); *G01R 33/093* (2013.01); *G01R 33/1269* (2013.01); *Y10T 29/4902* (2015.01)

(56) References Cited

U.S. PATENT DOCUMENTS

| | | | |
|---|---|---|---|
| 8,283,183 | B2 | 10/2012 | Ikeda et al. |
| 8,705,213 | B2 | 4/2014 | Butler et al. |
| 8,852,957 | B2 | 10/2014 | Ikeda |
| 9,121,887 | B2 | 9/2015 | Wang et al. |
| 2002/0060565 | A1* | 5/2002 | Tondra ................. G01N 27/745 324/260 |
| 2003/0175155 | A1 | 9/2003 | Charlton |
| 2004/0115922 | A1* | 6/2004 | Gruen ................. G01R 33/093 438/622 |
| 2005/0087000 | A1* | 4/2005 | Coehoorn ............. B82Y 25/00 73/53.01 |
| 2005/0106758 | A1 | 5/2005 | Fukumoto et al. |
| 2005/0244873 | A1 | 11/2005 | Ikeda et al. |
| 2006/0194327 | A1 | 8/2006 | Kahlan et al. |
| 2006/0291108 | A1 | 12/2006 | Sbiaa et al. |
| 2007/0231926 | A1 | 10/2007 | Ikeda et al. |
| 2008/0014651 | A1 | 1/2008 | Bangert |
| 2008/0311598 | A1 | 12/2008 | Vossenaar et al. |
| 2009/0009156 | A1 | 1/2009 | Duric |
| 2009/0021250 | A1 | 1/2009 | Ikeda |
| 2009/0104707 | A1 | 4/2009 | Wang et al. |
| 2009/0141410 | A1* | 6/2009 | Jogo ...................... B82Y 10/00 360/324.2 |
| 2009/0152127 | A1 | 6/2009 | Kaimori et al. |
| 2009/0181464 | A1 | 7/2009 | De Theije et al. |
| 2009/0206825 | A1 | 8/2009 | Boeve |
| 2009/0244788 | A1 | 10/2009 | Sato |
| 2010/0109657 | A1 | 5/2010 | Voegeli |
| 2010/0117641 | A1 | 5/2010 | Zhou |
| 2010/0160184 | A1 | 6/2010 | Suh et al. |
| 2010/0213934 | A1 | 8/2010 | Wang et al. |
| 2011/0156702 | A1 | 6/2011 | Kim et al. |
| 2011/0164335 | A1 | 7/2011 | Xue et al. |
| 2011/0211272 | A1 | 9/2011 | Butler et al. |
| 2011/0241664 | A1 | 10/2011 | Zhang |
| 2014/0174951 | A1 | 6/2014 | Beer et al. |
| 2014/0292318 | A1 | 10/2014 | Wang et al. |

FOREIGN PATENT DOCUMENTS

| | | |
|---|---|---|
| CN | 100343670 C | 10/2007 |
| CN | 101046464 A | 10/2007 |
| CN | 101313218 A | 11/2008 |
| CN | 101315429 A | 12/2008 |
| CN | 101379384 A | 3/2009 |
| CN | 101438162 A | 5/2009 |
| CN | 101443674 A | 5/2009 |
| CN | 101614700 A | 12/2009 |
| EP | 1469311 A1 | 10/2004 |
| JP | 2003524781 A | 8/2003 |
| JP | 2005513475 A | 5/2005 |
| JP | 2005315678 A | 11/2005 |
| JP | 2006208295 A | 8/2006 |
| JP | 2007514932 A | 6/2007 |
| JP | 2007212233 A | 8/2007 |
| JP | 2009008663 A | 1/2009 |
| JP | 2009536352 A | 10/2009 |
| JP | 2011204344 A | 10/2011 |
| WO | 03054523 A2 | 7/2003 |
| WO | 2005047864 A2 | 5/2005 |
| WO | 2006080558 A1 | 8/2006 |
| WO | 2007129284 A1 | 11/2007 |

OTHER PUBLICATIONS

Bae et al., "Chitosan Oligosaccharide-Stabilized Ferrimagnetic Iron Oxide Nanocubes for Magnetically Modulated Cancer Hyperthermia," ACS NANO, vol. 6, No. 6, American Chemical Society, 2012, pp. 5266-5273 (Applicant points out that, in accordance with MPEP 609.04(a), the 2012 year of publication is sufficiently earlier than the effective U.S. filing date and any foreign priority date of Mar. 6, 2014 so that the particular month of publication is not in issue.).

Butler et al., "Atomic spectrometry updated. Environmental analysis," Journal of Analytical Atomic Spectrometry, vol. 22, No. 2, The Royal Society of Chemistry Jan. 22, 2007, pp. 187-221.

Das et al., "An ultrasensitive universal detector based on neutralizer displacement," Nature Chemistry, vol. 4, Macmillan Publishers Limited, Jun. 2, 2012, pp. 642-650.

Ding et al., "[CoFe/Pt]xn Multilayer Films with a Small Perpendicular Magnetic," Journal of Applied Physics, vol. 97, 10J117, May 2005, 3 pp.

Ding et al., "Magneto-Resistive Read Sensor with Perpendicular Magnetic Anisotropy," IEEE Transactions on Magnetics, vol. 41, No. 2, Feb. 2005, 6 pp.

Ding et al., "Magnetoresistive Sensors with Perpendicular Magnetic Anistropy," Journal of Applied Physics, vol. 97, 10N704, May 2005, 3 pp.

Dong et al., "Quartz Crystal Microbalance Aptasensor for Sensitive Detection of Mercury(II) Based on Signal Amplification with Gold Nanoparticles," Sensors, vol. 12, May 29, 2012, pp. 7081-7094.

Ebdon et al., "Cold vapour atomic fluorescence spectrometry and gas chromatography-pyrolysis-atomic fluorescence spectrometry for routine determination of total and organometallic mercury in food samples," The Analyst, vol. 127, No. 8, Jul. 23, 2002, pp. 1108-1114.

Fortin et al., "Intercellular heating of living cells through Neel relaxation of magnetic nanoparticles," Biophysics letter, vol. 37, Jul. 20, 2007, pp. 223-228.

Freeman et al., "Chemiluminescent and Chemiluminescence Resonance Energy Transfer (CRET) Detection of DNA, Metal Ions, and Aptamer—Substrate Complexes Using Hemin/G-Quadruplexes and CdSe/ZnS Quantum Dots," Journal of the American Chemical Society, vol. 133, No. 30, American Chemical Society, Aug. 3, 2011, 10 pp.

Gaster et al., "Quantification of protein interactions and solution transport using high-density GMR sensor arrays" Nature Nanotechnology, Nature, vol. 6, Apr. 10, 2011, pp. 314-320.

Goda et al., "A hairpin DNA aptamer coupled with groove binders as a smart switch for a field-effect transistor biosensor," Biosensors and Bioelectronics, vol. 32, Dec. 24, 2011, pp. 244-249.

Graham et al., "Magnetoresistive-based biosensor and biochips," TRENDS in Biotechnology, vol. 22, No. 9, Science Direct, Jul. 2, 2004, 10 pp.

Grandjean et al., "Adverse Effects of Methylmercury: Environmental Health Research Implications," Environmental Health Perspectives, vol. 118, No. 8, Aug. 2010, pp. 1137-1145.

Guo et al., "Colorimetric detection of mercury, lead and copper ions simultaneously using protein-functionalized gold nanoparticles," Biosensors and Bioelectronics, vol. 26, Apr. 2, 2011, pp. 4064-4069.

Hodnik et al., "Toxin detection by surface plasmon resonance," Sensors, vol. 9, Open access, Feb. 26, 2009, pp. 1339-1354.

Jun et al., "Nanoscaling Laws of Magnetic Nanoparticles and Their Applicabilities in Biomedical Sciences," Accounts of Chemical Research, vol. 41, No. 2, Feb. 19, 2008, pp. 179-189.

Ke et al., "A facile and highly sensitive probe for Hg(II) based on metal-induced aggregation of ZnSe/ZnS quantum dots," Nanoscale, vol. 4, No. 16, The Royal Society of Chemistry, Aug. 21, 2012, 8 pp.

Kim et al., "A Drug-Loaded Aptamer—Gold Nanoparticles Bioconjugate for Combined CT Imagine and Therapy of Prostate Cancer," ACS NANO, vol. 4, No. 7, American Chemical Society, 2010, pp. 3689-3696 (Applicant points out that, in accordance with MPEP 609.04(a), the 2010 year of publication is sufficiently earlier

(56) References Cited

OTHER PUBLICATIONS than the effective U.S. filing date and any foreign priority date of Mar. 6, 2014 so that the particular month of publication is not in issue.).

Koets et al., "Rapid DNA multi-analyte immunoassay on magneto-resistance biosensor," Biosensors and Bioelectronics, vol. 24, ScienceDirect, Oct. 8, 2008, pp. 1893-1898.

Kong et al., "Magnetically Vectored Nanoscapsules for Tumor Penetration and Remotely Switchable On-Demand Drug Release," Nano Letters, vol. 10, No. 12, American Chemical Society, Nov. 1, 2010, pp. 5088-5092.

Langford et al., "Toxicity of mercury," Journal of Human Hypertension, vol. 13, Stockton, Jun. 10, 1999, pp. 651-656.

Lee et al., "Colorimetric Detection of Mercuric Ion (Hg) in Aqueous Media using 2+ DNA-Functionalized Gold Nanoparticles," Angewandte Chemie International Edition, vol. 46, No. 22, WILEY-VCH, 2007, pp. 4093-4096 (Applicant points out that, in accordance with MPEP 609.04(a), the 2007 year of publication is sufficiently earlier than the effective U.S. filing date and any foreign priority date of Mar. 6, 2014 so that the particular month of publication is not in issue.).

Li et al., "Detection of Adenosine Triphosphate with an Aptamer Biosensor Based on Surface-Enhanced Raman Scattering," Analytical Chemistry, vol. 84, No. 6, American Chemical Society, Mar. 20, 2012, 6 pp.

Li et al., "Elimination efficiency of different reagents for the memory effect of mercury using ICP-MS," Journal of Analytical Atomic Spectrometry, vol. 21, No. 1, Technical Note, The Royal Society of Chemistry, Nov. 16, 2005, pp. 94-96.

Lin et al., "A Self-Powered Triboelectric Nanosensor for Mercury Ion Detection," Angewandte Chemie International Edition, vol. 52, Wiley Online Library, 2013, pp. 5065-5069 (Applicant points out that, in accordance with MPEP 609.04(a), the 2013 year of publication is sufficiently earlier than the effective U.S. filing date and any foreign priority date of Mar. 6, 2014 so that the particular month of publication is not in issue.).

Loureiro et al., "Magnetoresistive detection of magnetic bead flowing at high speed in microfluidic channels," IEEE Transactions on Magnetics, vol. 45, Oct. 10, 2009, pp. 4873-4876.

Mamiya et al., "Hyperthermic effects if dissipative structure of magnetic nanoparticles in large alternating magnetic fields," National Institute for Materials Science, Nov. 15, 2011, pp. 1-7.

Manteca et al., "GMR sensors: Magnetoresistive behavior optimization for biological detection by means of superparamagnetic nanoparticles," Biosensors and Bioelectronics, vol. 26, ScienceDirect, Nov. 24, 2010, pp. 3705-3709.

Martinez et al., "Diagnostics for the Developing World: Microfluidic Paper-Based Analytical Devices," Analytical Chemistry, vol. 82, No. 1, American Chemical Society, Jan. 1, 2010, 6 pp.

Martins et al., "Femtomolar limit of detection with a magnetoresistive biochip," Biosensors and Bioelectronics, vol. 24, Feb. 6, 2009, pp. 2690-2695.

Morel et al., "The chemical cycle and bioaccumulation of mercury," Annual review of ecology and systematics, vol. 29, 1998 pp. 543-566.

Mulvaney et al., "Magnets tackle kinetic questions," Nature Nanotechnology, vol. 6, Nature, May 2011, pp. 266-267.

Mulvaney et al., "Rapid, femtomolar bioassays in complex matrices combining microfluids and magnetoelectronics," Biosensors and Bioelectronics, vol. 23, ScienceDirect, Apr. 8, 2007, pp. 191-200.

Nam et al., "Nanoparticle-Based Bio-Bar Codes for the Ultrasensitive Detection of Proteins," Science, vol. 301, No. 5641, Reports, Sep. 26, 2003, pp. 1884-1886.

Ono et al., "Highly selective oligonucleotide-based sensor for mercury(II) in aqueous solution," Molecular sensors, vol. 43, Angewandte, 2004, pp. 4300-4302.

Osterfeld et al., "Multiplex protein assays based on real-time matmetic nanotag sensing," Proceedings of the National Academy of sciences of the United States of America, vol. 105, PNAS, Dec. 30, 2008, pp. 20637-20640.

Rajkovic et al., "Immunoquantitative Real-Time PCR for Detection and Quantification Of *Staphylococcus aureus* Enterotoxin Bin Foods," Applied and Environmental Microbiology, vol. 72, No. 10, American Society for Microbiology, Oct. 2006, pp. 6593-6599.

Rosi et al., "Oligonucleotide-Modified Gold Nanoparticles for Intracellular Gene Regulation," Science, vol. 312, May 19, 2006, pp. 1027-1030.

Salgan et al., "Zeta potential and isoelectric points of biomolecules: The effects of ion types and ionic strengths," International Journal of Electrochemical science, vol. 7 Dec. 1, 2012, pp. 12404-12414.

Schotter et al., "Development of a magnetic lab-on-a-chip for point-of-care sepsis diagnosis," Magnetism and Magnetic Materials, vol. 321, ScienceDirect, Feb. 21, 2009, pp. 1671-1675.

Shao et al., "Protein typing of circulating microvesicles allows real-time monitoring of glioblastoma therapy," Nature Medicine, vol. 18, No. 12, Technical Reports, Nov. 11, 2012, pp. 1835-1843.

Srinivasan et al., "A detection system based on giant magnetoresistive sensors and high-moment matmetic nanoparticles demonstrates zeptomole sensitivity: Potential for personalized medicine," Biosensors, vol. 48, Andgewandte, 2009, pp. 2763-2767 (Applicant points out that, in accordance with MPEP 609.04(a), the 2009 year of publication is sufficiently earlier than the effective U.S. filing date and any foreign priority date of Mar. 6, 2014 so that the particular month of publication is not in issue.).

Stenberg et al., "Kinetics of antigen-antibody reactions at solid-liquid interfaces," Journal of Immunological methods, vol. 113, Jun. 29, 1988, pp. 3-15.

Tang et al., "Design fabrication, and performance of spin-valve read heads for magnetic recording applications," Journal of research and development, vol. 42, Jan. 1, 1998, pp. 103-116.

Tu et al., "Real-time measurements of Brownian relaxation of magnetic nanoparticles by a mixing-frequency method," Applied Physics letters, vol. 98, May 26, 2011, pp. 1-3.

Vasimalai et al., "Mercaptothiadiazole capped gold nanoparticles as fluorophore for the determination of nanomolar mercury (II) in aqueous solution in the presence of 50000-fold major interferents," Analyst, vol. 137, No. 14, The Royal Society of Chemistry, Jul. 21, 2012, pp. 3349-3354.

Wang et al., "Magnetic Detection of Mercuric Ion Using Giant Magnetoresistive Based Biosensing System," Analytical Chemistry, American Chemical Society, Mar. 24, 2014, 23 pp.

Wang et al., "Surface modification for protein and DNA immobilization onto GMR biosensor," IEEE transactions on magnetics, vol. 49, Jan. 1, 2013, pp. 296-299.

Wen et al., "Self-Powered Sensor for Trace Hg 2+ Detection," Analytical Chemistry, vol. 83, No. 10, American Chemical Society, May 15, 2011, 5 pp.

Xia et al., "Colorimetric detection of DNA, small molecules, proteins, and ions using unmodified gold nanoparticles and conjugated polyelectrolytes," Proceedings of the National Academy of sciences of the United States of America, vol. 107, PNAS, Jun. 15, 2010, pp. 10837-10841.

Xue et al., "One-step, room temperature, colorimetric detection of mercury (Hg2+) using DNA/nanoparticle conjugates," Journal of the American Chemical Society, vol. 130, JACS, Sep. 6, 2007, pp. 3244-3245.

Zheng et al., "Multiplexed electrical detection of cancer markers with nanowire sensor arrays," Nature Biotechnology, The Science and Business of Biotechnology, vol. 23, No. 10, Sep. 18, 2005, pp. 1294-1301.

Zhi et al., " Quick genotyping detection of HBV by giant magnetoresistive biochip combined with PCR and line probe assay," Lab on a chip, vol. 12, Miniaturisation for chemistry, physics, biology, materials science and bioengineering, Feb. 21, 2012, pp. 741-745.

U.S. Appl. No. 14/676,620, by Jian-Ping Wang, filed Apr. 1, 2015.

Translation of Amended Claims from counterpart Japanese Application No. 2014-530904, filed Aug. 6, 2015, 3 pp.

Wu et al., "Research development of spin valve giant magnetic resistance biosensors with magnetic labels," Transducer and Microsystem Technologies, Nov. 26, 2007, pp. 13-16 (Translation provided for only the Abstract).

(56) References Cited

OTHER PUBLICATIONS

First Office Action and Search Report, and translation thereof, from counterpart Chinese Application No. 201280050034.0, dated Apr. 25, 2016, 9 pp.

Notice of Reasons for Rejection, and translation thereof, from counterpart Japanese Application No. 2014-530904, dated Apr. 7, 2015, 8 pp.

Zheng et al., "Switch-free read operation design and measurement of magnetic tunnel junction magnetic random access memory arrays," Applied Physics Letters, vol. 79, No. 17, Oct. 22, 2001, 4 pp.

Baselt et al., "A Biosensor Based on Magnetoresistance Technology," Biosensors Bioelectronics, vol. 13 (7-8), Oct. 1998, pp. 731-739.

deBOER et al., "An Integrated and Sensitive Detection Platform for Magneto-Resistive Biosensors," Biomedical Sensor Systems, vol. 22 (9-10), Apr. 15, 2007, pp. 2366-2370.

Gaster et al., "Matrix-Insensitive Protein Assays Push the Limits of Biosensors in Medicine," Nature Medicine, vol. 15 (11), Nov. 2009, pp. 1327-1332.

Graham et al., "Single Magnetic Microsphere Placement and Detection On-Chip Using Current Line Designs with Integrated spin Valve Sensors: Biotechnological Applications," Journal of Applied Physics, vol. 91 (10), May 15, 2002, pp. 7786-7788.

Janssen et al., "On-Chip Manipulation and Detection of Magnetic Particles for Functional Biosensors," Biosensors Bioelectronics, vol. 23 (6), Jan. 2008, pp. 833-838.

Llandro et al., "Magnetic Biosensor Technologies for Medical Applications: A Review," Medical and Biological Engineering & Computing, vol. 48 (10), Jun. 24, 2010, pp. 977-998.

Li et al., "Nanomagnetic Competition Assay for Low-Abundance Protein Biomarker Quantification in Unprocessed Human Sera," Journal of American Chemical Society, vol. 132 (12), Mar. 1, 2010, pp. 4388-4392.

Martins et al., "Challenges and Trends in the Development of a Magnetoresistive Biochip Portable Platform," Journal Magnetism and Magnetic Materials, vol. 322 (9-12), May 2010, pp. 1655-1663.

Rife et al., "Design and Performance of GMR Sensors for the Detection of Magnetic Microbeads in Biosensors," Sensors and Actuators A: Physical, vol. 107 (3), Jul. 25, 2003, pp. 209-218.

Schotter et al., "Comparison of a Prototype Magnetoresistive Biosensor to Standard Fluorescent DNA Detection," Biosenssors Bioelectronics, vol. 19 (10), May 2004, pp. 1149-1156.

Srinivasan et al., "A Detection System Based on Giant Magnetoresistive Sensors and High-Moment Magnetic Nanoparticles Demonstrates Zeptomole Sensitivity: Potential for Personalized medicine," Angew. Chem., vol. 121, Mar. 2009, pp. 2802-2805.

Tamanaha et al., "Magnetic Labeling, Detection, and System Integration," Biosensors Bioelectronics, vol. 24 (1), Feb. 2008, pp. 1-13.

Invitation to Pay Additional Fees from Corresponding International Application No. PCT/US2012/055618, dated Sep. 14, 2012, 4 pp.

International Search Report and Written Opinion of Corresponding International Application No. PCT/US2012/055618, dated Mar. 6, 2013, 16 pp.

International Preliminary Report on Patentability from Corresponding International Application No. PCT/US2012/055618, dated Mar. 18, 2014, 9 pp.

\* cited by examiner

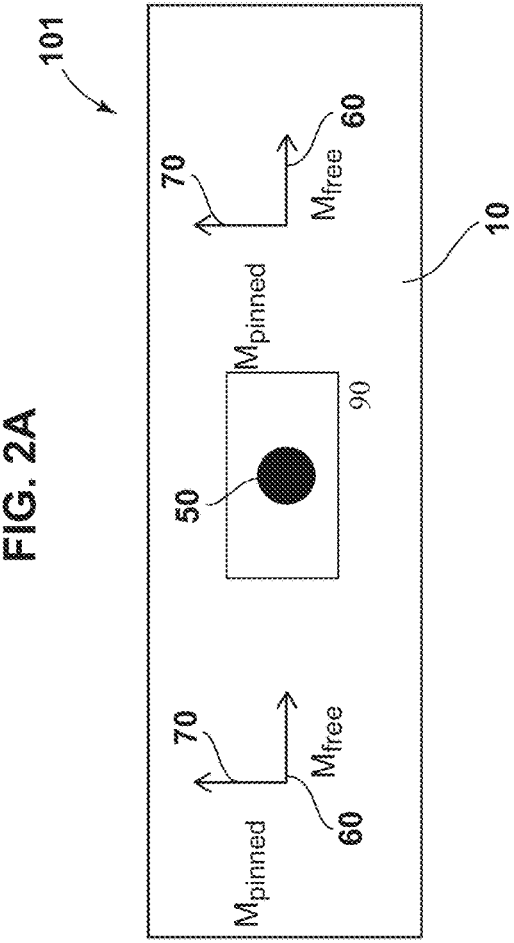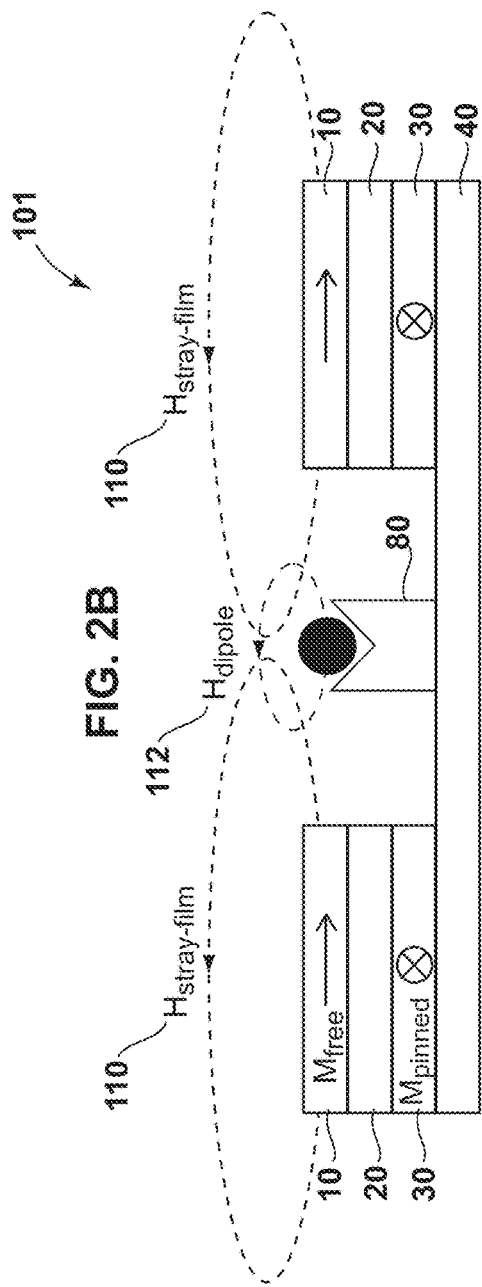

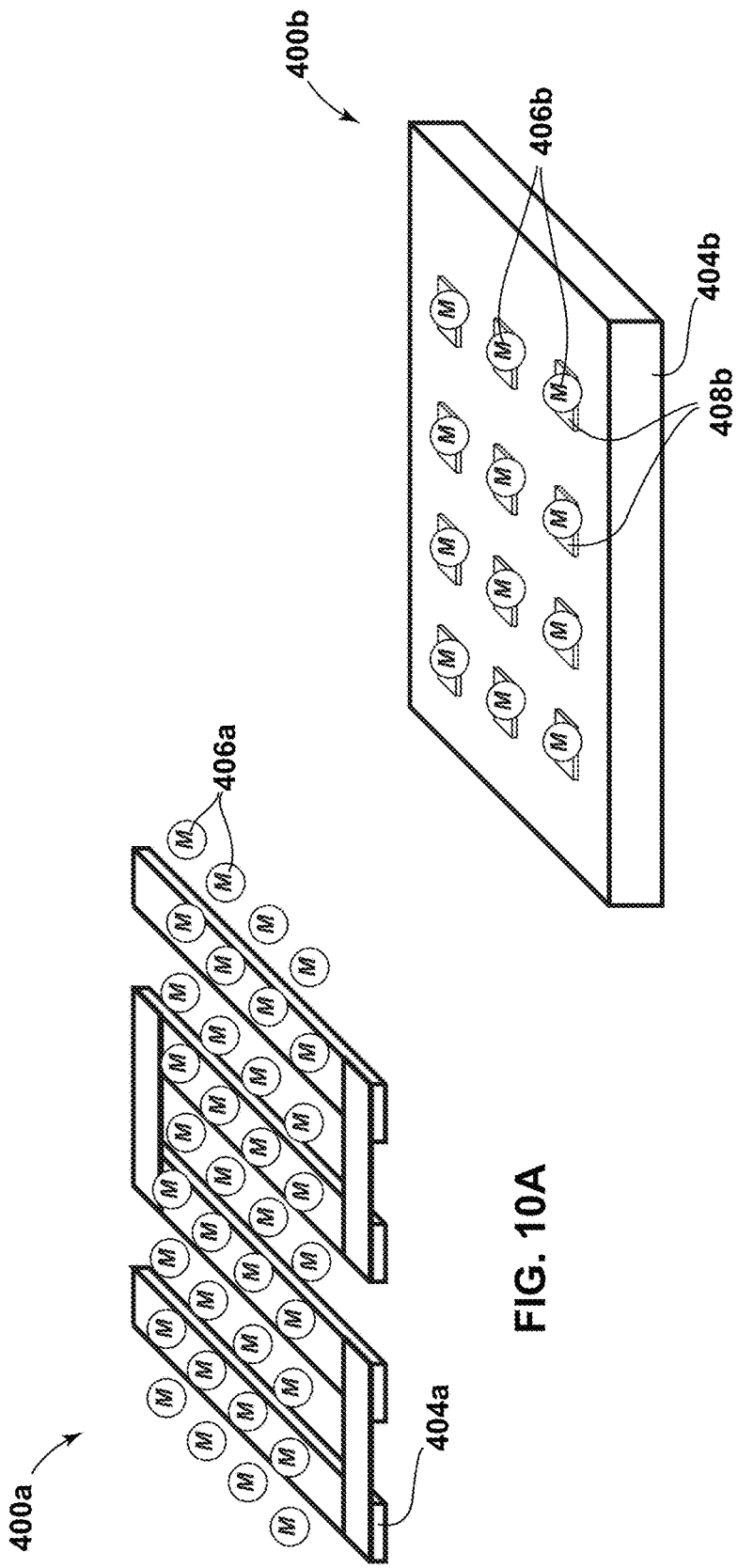

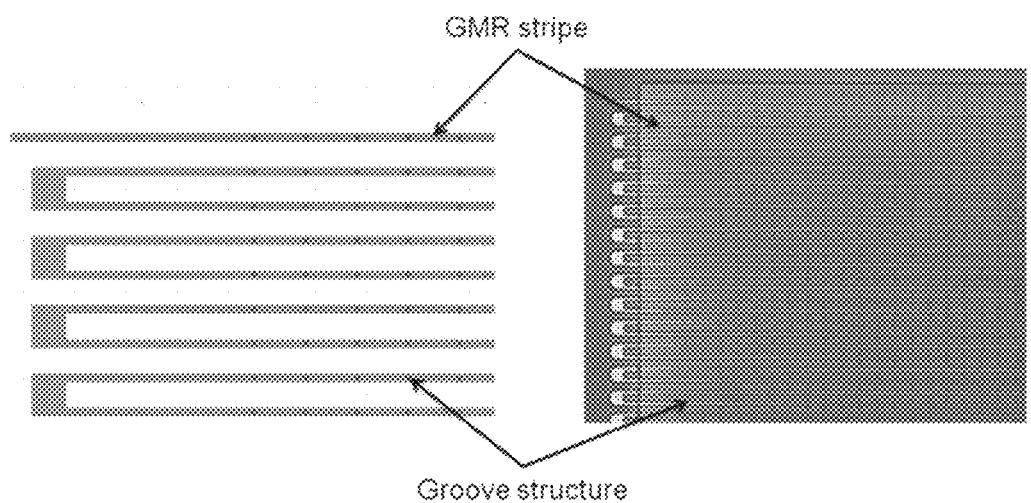
FIG. 20
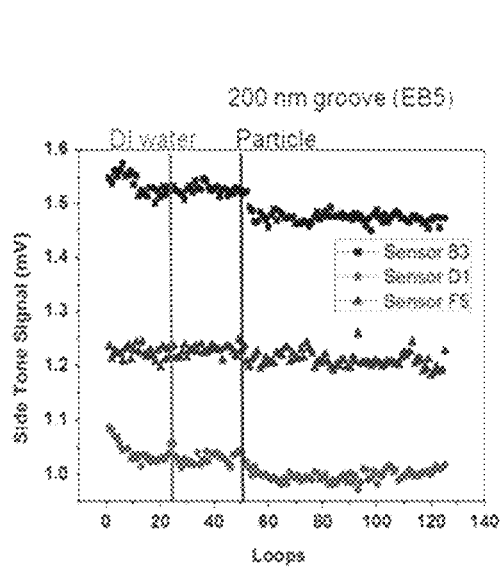 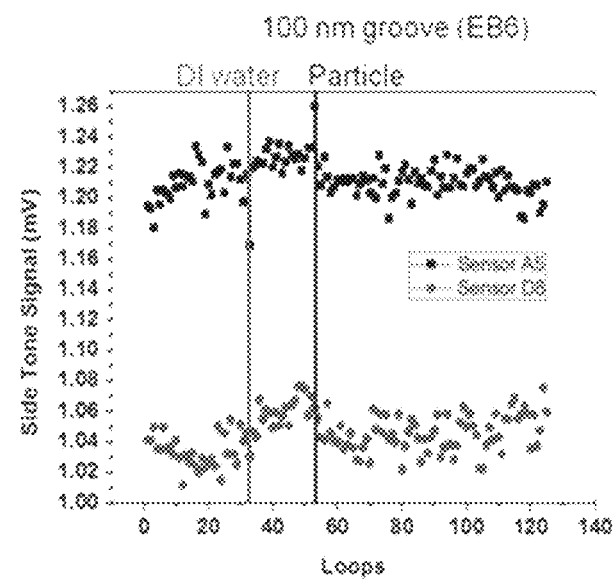
FIG. 21          FIG. 22

EXTERNAL FIELD—FREE MAGNETIC BIOSENSOR

This application claims the benefit of application No. 61/534,636, filed Sep. 14, 2011, the entire content of which being incorporated herein by reference.

TECHNICAL FIELD

This invention relates to magnetic biosensors.

BACKGROUND

Bioassays and biosensors that detect and quantify biomolecules at ultra-low quantity, with point-of-care settings, are of great need in many fields, including basic medical science, disease control and diagnostics, drug discovery and environment monitoring. Bioassays can be used for disease or pathogen detection based on the principle of specific interactions between biological components Antibody-antigen interaction is one example of a specific interaction between biomolecules which can be used. Some other examples of biological interactions include interactions between oligonucleotides, such as DNA-DNA or RNA-RNA interaction, small-molecule-biomolecule interactions, aptamer-biomolecule interactions, protein interactions, and others.

Magnetic biosensors include giant magnetoresistive (GMR) sensors, magnetic tunnel junction (MTJ) sensors, Hall biosensors or Giant magneto impedance (GMI) biosensors. Magnetic biosensing, which combines the magnetic biosensor and magnetic nanoparticles (MNPs), is a field which has been intensively studied. In existing magnetic biosensing schemes, when the targeted biomolecues are present, they bond to the biologically-functionalized surface of an individual magnetic field sensor or a sensor-array. Functionalized MNPs bond to these targeted biomolecules. The dipole field from the specifically bound magnetized MNPs will change the overall effective magnetic field on the sensing layer of the magnetic biosensor. This causes the change of the magnetization configuration of the magnetic biosensor, thus generating an electrical signal from the biosensor, which can be quantitatively correlated with the number of the MNPs.

Conventionally, as shown in FIGS. 7 and 8, a powerful, externally-applied magnetic field is required and operates as the exclusive source for magnetizing the MNPs. Hence, in conventional magnetic biosensing schemes, the necessity for an external magnetic field generator downplays the promised portability feature for magnetic biosensors and also increases the power consumption of the whole system.

Generating a magnetic field from built-in current lines on the biosensor has also been proposed for magnetizing the MNPs. This can eliminate the usage of an external electromagnet. However, the requirement for large power consumption still exists. The presence of a large current on a sensing chip, such as tens of milliamperes, is typically required to produce a large enough magnetic field for magnetizing the MNPs. Such a large current causes heating effects and may also result in a dielectric break down between the protection layer and the biological sample.

SUMMARY

In general, magnetic biosensing techniques are described that utilize stray field from the magnetic biosensor to magnetize and bind magnetic labels, such as magnetic nanoparticles (MNPs) or slightly larger magnetic particles including magnetic microbeads, to biological molecules. The techniques may reduce or eliminate the usage of any external magnetic field generator, e.g., electromagnets or current lines. The techniques may utilize a specific patterned structure, e.g. a groove, in the magnetic biosensor. The specific patterned structure may be fabricated using an ion milling and other lithograph processes.

More specifically, a magnetic nanoparticle detection scheme is described that avoids the requirement of any externally generated magnetic field. Traditional magnetic biosensing schemes employ an externally applied magnetic field generator to magnetize the superparamagnetic MNPs. This results in extra power consumption, which may be a critical factor for point-of-care applications adopting magnetic biosensors. The detection scheme described herein introduces a patterned groove structure in the biosensor which utilizes the stray magnetic fields from the magnetic device to magnetize the MNPs.

An example is described below based on a spin-valve giant magnetoresistance (GMR) sensing device. For this structure, the stray field from the free layer and the pinned layer is used to magnetize the MNPs, which locate inside the groove. Micromagnetic simulations have been performed to calculate the signal level of this detection scheme. The simulation produced a maximum signal of $8.9 \times 10^{-5}$ magnetoresistive ratio (MR) change from one iron oxide magnetic nanoparticle with 8 nm in radius. This signal level is high enough for the detection of about 10 such nanoparticles if using the state-of-art electronic circuit for signal processing. This new detection scheme is not limited to GMR devices and is applicable for use with other spintronic and magnetic sensing devices such as magnetic tunnel junction (MTJ) devices, Hall sensors with a sandwiched structure, and giant magneto impendence (GMI) devices.

The biosensor may utilize, for example, a GMR sensing device having the spin valve structure, an MTJ sensing device having the spin valve structure, a GMI sensing device having the spin valve structure or a Hall sensing device having the spin valve structure. The biosensor may include a magnetic sensing device that has a soft magnetic layer underneath a Hall sensing layer. In this example, the soft magnetic layer responds to the sensing current and generates the magnetic field. For some magnetic sensing schemes, like the Hall sensor or a semiconductor layer, a single layer may only be needed. A single soft magnetic layer underneath the sensing layer may be utilized to generate the magnetic field.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 2A and 2B depict, from the top-down and profile views, respectively, an example magnetic biosensor using the proposed biosensing scheme which includes a groove structure formed on the biosensor

FIG. 4A graphs the signal from the sensor using a fixed groove width of 100 nm and a varying groove length. FIG. 4B graphs the signal from the sensor using a fixed groove width of 200nm and a vaging groove length.

FIG. 9A depicts an example magnetic biosensor combined with a handheld device. FIG. 9B illustrates aspects of the handheld device.

FIGS. 10A and 10B illustrate two example configurations of the proposed magnetic biosensor. FIG. 10A shows a strip-type magnetic biosensor in which a grooved pattern is formed to include a pluralig of parallel linear grooves surrounded by magnetic biosensing strips. FIG. lOB shows a second example proposed magnetic biosensor in which the magnetic biosensing substrate is patterned with notches.

FIG. 20 shows the layout and dark field microscope images used in creating a strip-type biosensor using the proposed magnetic biosensing scheme.

FIGS. 21 and 22 show the real-time signals from an example strip-type sensor using the proposed magnetic biosensing scheme as magnetic labels were introduced into the system. FIG. 21 shows the results for a sensor with 200nm grooves and FIG. 22 shows the results for a sensor with 100nm grooves.

DETAILED DESCRIPTION

For the ease of description, the term magnetic nanoparticle will be used in the description to refer to the magnetic labels that attach to the biological molecules. However, this convention does not limit the magnetic labels only to particles traditionally described as nanoparticles. Other sizes of magnetic particles, such as microbeads, are also contemplated by the invention. One of skill in the art would know to adjust the size of the various components of the device to accept other sized particles.

Figure 1A:
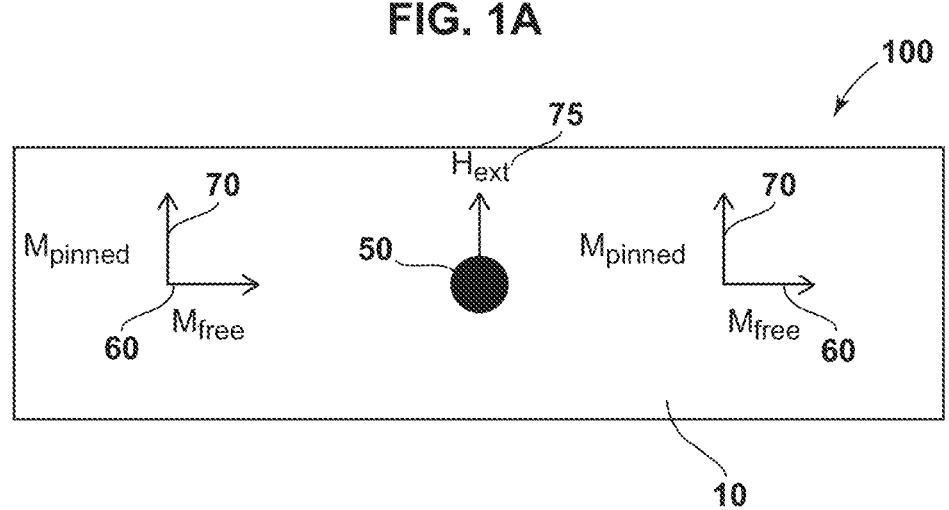
FIGS. 1A and 1B depict an example of a conventional magnetic biosensor from the top-down view and profile view, respectively.
Figure 1B:
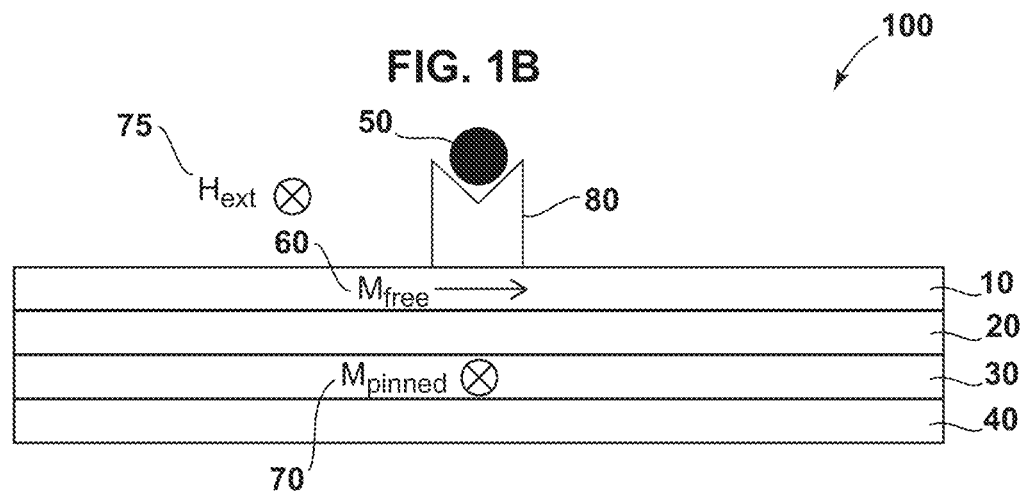

FIGS. 1A and 1B, from the top-down and cross sectional views, respectively, show a conventional magnetic biosensing scheme using a spin valve structure. As shown in FIGS. 1A and 1B, a magnetic nanoparticle (MNP) 50 is bound to the surface of magnetic biosensor 100 through biological bond 80. The magnetic biosensor 100 may be formed from a free layer 10, a spacer layer 20, and a pimped layer 30. Other embodiments may include a substrate layer 40 while still other embodiments may include more or fewer layers. Pinned layer 30 may contain a magnetic field. Reference number 70 shows an example direction of a magentic field in pinned layer 30. Free layer 10 may also contain a magnetic field. Reference number 60 shows an example direction of a magnetic field in free layer 10. In a conventional configuration, an external magnetic field 75 is needed in order to magnetize the superparamagnetic MNP 50. Once the MNP 50 becomes magnetized, the MNP 50 generates a dipole magnetic field 112 (shown in FIG. 2B) which exerts a magnetic force on the free layer 10 of the magnetic biosensor 100.

Figure 7:
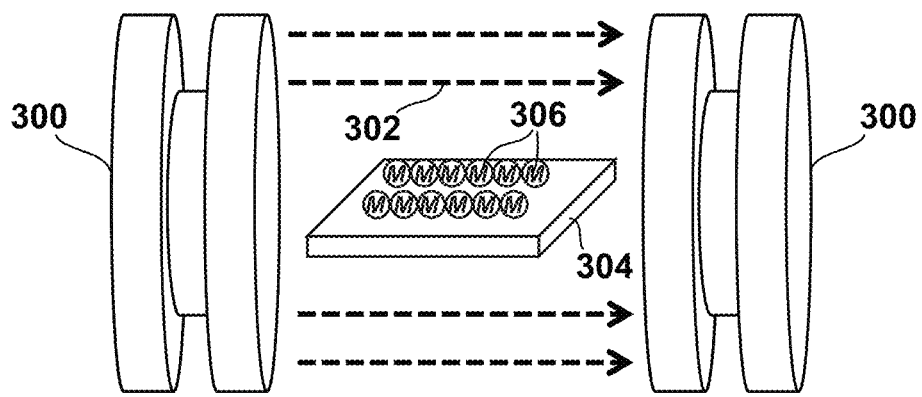
FIG. 7 illustrates a prior art biosensing scheme that uses an external magnetic field to magnetize the magnetic labels.
Figure 8:
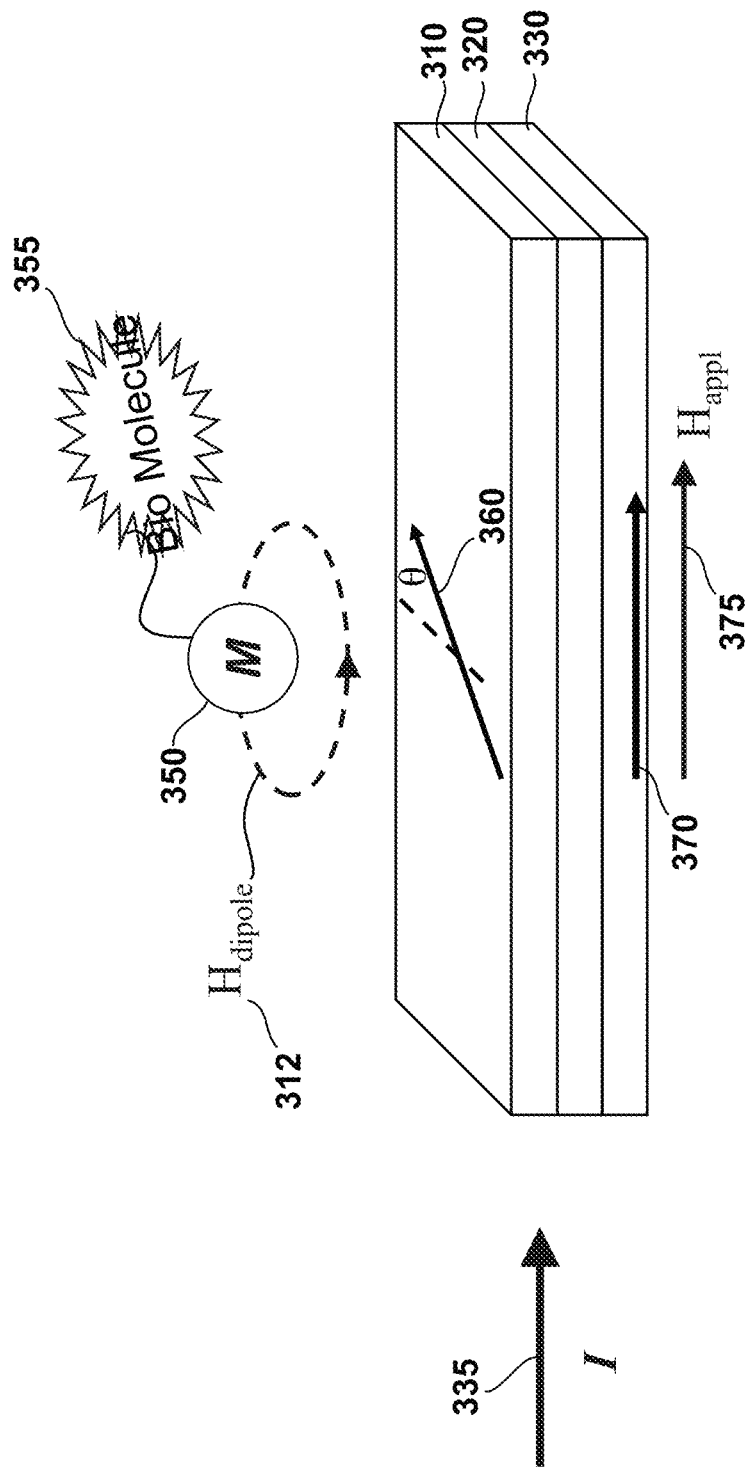
FIG. 8 illustrates a conventional (prior art) magnetic biosensor.

For example, FIGS. 7 and 8 further illustrate a conventional biosensing scheme. FIG. 7 describes a magnetic biosensor 304 containing MNPs 306 positioned in a magnetic field generator 300. The magnetic field generator 300 generates an externally applied magnetic field 302, which is necessag in conventional biosensing schemes to magnetize the MNPs 306. FIG. 8 shows a close up of an MNP 350 interacting with a conventional biosensing scheme. MNP 350 is attached to a biological molecule 355. The conventional magnetic biosensor displayed in FIG. 8 includes a free layer 310, a spacer layer 320, and a pinned layer 330. The externally applied magnetic field reguired to magnetize the MNP 350 is demonstrated by arrow 375. The externally applied magnetic field 375 may result from use of an electromagnet or other magnet gnot shown). The field 375 may also result from the use of current 335 running through built in current lines on the biosensor (not shown). Once the MNP 350 has been magnetized, its dipole magnetic field 312 interacts with the free layer 310, deflecting the direction of the free layer's 310 magnetic field 360.

Referring back to FIG. 1, before the MNP 50 bonds to the sensor surface, the effective field $H_{eff}$ on the free layer 10 is:

$$H_{eff}=H_{ext}+H_{stray\text{-}pinned} \quad (1),$$

where $H_{ext}$ is the external applied magnetic field 75 and $H_{stray\text{-}pinned}$ is the stray field from the pinned layer 30. After bonding to the surface of the magnetic biosensor 100 through a biological bond 80, the MNP 50 is magnetized by the externally applied magnetic field 75. In the conventional device, both of the stray magnetic fields (shown as 110 in FIG. 2B) from the free layer 10 and pinned layer 30 are very small and may be ignored for the conventional magnetic biosensing scheme. The magnetic charges from the free layer 10 (two ends of the long axis of the sensor) are far from most of the bonded MNPs 50 because of the large dimension of the sensor along the long axis. The magnetic charges from the pinned layer 30 (two ends of the short axis of the sensor) are far from most of bonded MNPs 50 because of the distance from the pinned layer 10 to the top surface of magnetic biosensor 100. Due to the superparamagnetic property of the MNPs 50, with an externally applied magnetic field 75 H, its magnetization can be expressed as:

$$M = M_s \times L\left(\frac{m_0 \mu_0 H}{k_B T}\right), \quad (2)$$

where $M_s$ is the saturation magnetization, $m_0$ is the magnetic moment of a single particle, $\mu_0$ is the magnetic permeability of vacuum, H is the externally applied magnetic field 75, $k_B$ is the Boltzmann constant, T is the absolute temperature, and L is the Langevin function. Accordingly, the dipole magnetic field 112 from the MNP 50 on the free layer 10 can be written as:

$$H_{dipole} = \frac{3(m \cdot r)r}{r^5} - \frac{m}{r^3}, \quad (3)$$

where m is the magnetic moment of the MNP, r is space vector from the center of the MNP 50 to the free layer 10. Therefore, the effective field on the free layer 10 is expressed as:

$$H_{eff} = H_{ext} + H_{stray-pinned} + H_{dipole} \quad (4),$$

The change of $H_{eff}$ on the free layer 10 before and after the MNP 50 bonding will change the orientation of the free layer magnetization $M_{free}$ which leads to an electrical signal change of the magnetic biosensor 100.

FIGS. 2A and 2B, from the top-down and cross sectional views, respectively, illustrate an example magnetic biosensor 101 in accordance with this disclosure. For example, magnetic biosensor 101, as described in further detail below, may be utilized with an external-magnetic-field-free detection scheme in which a magnetic field created by the biosensor is the sole magnetic field for magnetizing and bonding MNPs. As anothe example, biosensor 101 may be used in the presence of an external magnetic field, in which case the magnetic field created by the biosensor aids and improves the detection efficiency and accuracy of the biosensor. In the example of FIGS. 2A and 2B, a groove structure 90 is purposely created on the magnetic sensor 101. MNPs 50 bind to the sensor 101 in the groove 90, through a biological bond 80, where the magnetic forces from both free layer 10 and pinned layer 30 are close to the MNP 50.

The biological bond 80 is formed between the MNP 50 and a biological substance (not depicted) adhered to the magnetic biosensor 101. The biological substance may be adhered to the magnetic biosensor 101 in various locations. For example, the biological substance may only be adhered to the biosensor 101 within the groove. In other embodiments, the biological substance is adhered to the biosensor 101 all over, including inside groove and on the surface of the sensor 101. Other patterns of adhesion for the biological substance may be used as well. Since the MNP 50 will only form biological bond 80 with the biological substance, the MNP 50 will only bind to the magnetic biosensor 101 where the biological substance is adhered to the sensor 101.

FIGS. 2A and 2B depict a single MNP 50 bound within the groove 90 of magnetic biosensor lOl. Within the groove 90, the stray magnetic fields 110 from the free and pinned layers 10 and 30, $H_{stray-film}$, are strong. In this configuration, before the MNP 50 bonding, the effective field on the free layer 10 is only the stray magnetic field from the pinned layer 30, without the presence of the external applied field 75:

$$H_{eff} = H_{stray-pinned} \quad (5),$$

The MNP 50, after bonding in the groove, will be magnetized by the stray magnetic fields 110 from both the free and pinned layers 10 and 30. Hence its magnetization can be expressed by:

$$M = M_s \times L\left(\frac{m_0 \mu_0 H_{stray-film}}{k_B T}\right), \quad (6)$$

where $H_{stray-film}$ is the stray magnetic fields 110 from the free and pinned layers 10 and 30 of the magnetic biosensor. Combining the stray magnetic fields 110 with the dipole magnetic field 112 that is generated by the MNP 50, the effective field on the free layer 10 after the MNP 50 bonding is expressed as:

$$H_{eff} = H_{stray-pinned} + H_{dipole} \quad (7),$$

Therefore, the difference of the effective field on the free layer 10 changes the magnetization configuration of the free layer 10. By utilizing the strong stray fields from the free and pinned layers 10 and 30 to magnetize the MNP 50, the external applied field (reference number 75 in FIGS. 1A and 1B) is no longer needed in this novel detection scheme.

Although in some embodiments the externally applied magnetic field 75 is not needed, other embodiments still utilize the externally applied magnetic field 75. Using an externally applied magnetic field 75 in conjunction with the biosensing scheme described herein, and illustrated through example biosensor 101, can enhance the signal produced by the system. The externally applied magnetic field 75 in conjunction with the stray magnetic fields 110 from the free and pinned layers 10 and 30 increase the magnetization of the MNPs 50, thereby resulting in a greater signal than would be achieved using only the external magnetic field 75 or the stray magnetic fields from the free and pinned layers 10 and 30 to magnetize the MNPs 50.

In various examples, the free layer 10 typically ranges from 1 to 10 nm in thickness, the spacer layer 20 may generally be 1-10 nm in thickness, while the pinned layer 30 typically ranges from 5 to 50 nm. Although not shown, the substrate 40 may take the form of one or more layers including a physical substrate, an adhesion layer, a seed layer, and underlayer spacing and insulation layers, and the like.

Figure 3:
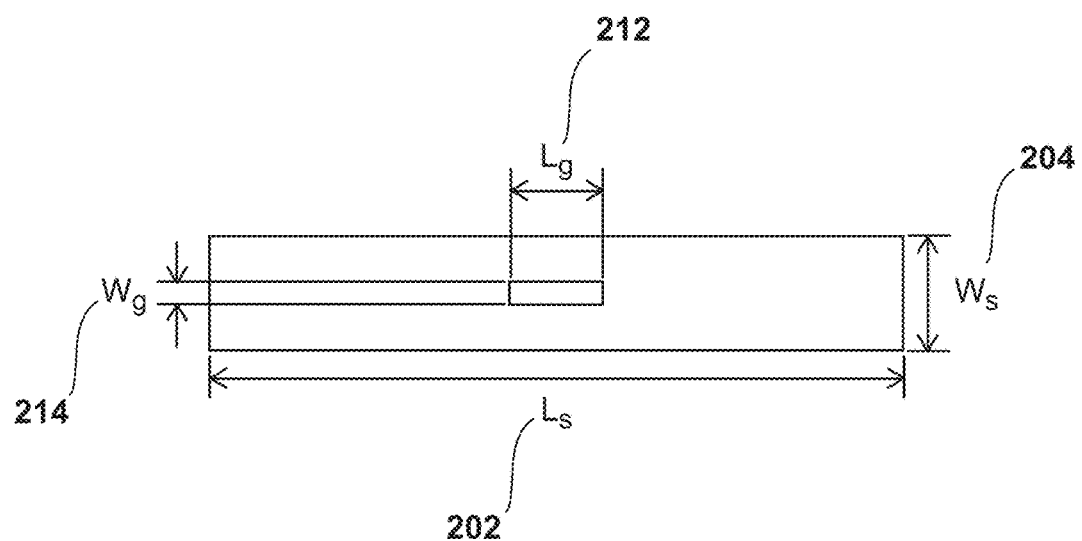
FIG. 3 illustrates an example magnetic biosensor with a groove structure and defines dimensions for the biosensor structure and the groove structure.

FIG. 3 illustrates a top-down view of an example of the shape the groove 90 may take in relation to the overall magnetic biosensor 101. The length 202 of the magnetic biosensor 101 can be denoted as $L_s$ and the width 204 of the magnetic biosensor 1O1 can be denoted as $W_s$. The length 212 of the groove 90 can be denoted as $L_g$ and the width 214 of the groove 90 can be denoted as $W_g$. In some examples, the groove 90 is formed with a width that accommodates binding of multiple MNPs (e.g., two to three times the diameter of the particles to be bound). For example, the magnetic biosensor 101 may be designed to bond with MNPs 50 which typically range from a few nanometers to less than 100 nanometers and more typically on the order of 1 to 10 nanometers. In such an example, the groove 90 may be formed between 50 to 300 nanometers in width. In other example magnetic biosensors 101, the groove 90 may have a width of several microns, (e.g., 1-5 microns) in order to allow binding of larger magnetic particles, which may be on the order of sub-micron up to two microns (e.g. 100 to 200 nanometers). In another example, the magnetic biosensor 101 may be configured to bond magnetic objectives with shapes different from spheres or cubes. Other possible shapes include rod or wire or tube shapes. The size of these other shapes may be on the order of sub-micron in length and width (e.g. 50 nm-1000 microns). In those examples, the groove 90 may have a width and a length of several times larger than the dimensions of the magnetic objectives. Although FIG. 3 depicts a rectangular groove 90, groove 90 may take the form of other geometric shapes, for example, circular, oval, triangular, and trapezoidal.

Further, the groove 90 may be formed with sufficient depth to contain the biological substance so that biological bond 80 between the MNP 50 and the biological substance still occurs within the groove 90. The groove 90 may be formed to extend through the free layer 10 and a portion of the pinned layer 30, e.g., to the underlying substrate layer 40. In this case, the groove 90 may range from 1 to over 100 nanometers in depth. Moreover, the groove 90 may be formed so as to have a depth such that, upon the MNPs 50 becoming biologically bound to the biological substance within the groove 90, the center of the MNPs 50 may be generally vertically aligned with a center of the free layer 10, as shown in FIG. 2B. In general, the groove 90 may be formed such as to have a large bonding surface with the MNPs 50 without compromising the magnetic performance of the free layer 10 and the pinned layer 30.

In other example biosensors, grooves 90 may be filled or partially filled with material (e.g. $SiO_2$, $Al_2O_3$, SiN, etc). Thus, in some examples, the surface of the groove areas 90 and the surface of the magnetic biosensor 101 may be at the same level or close to the same level. The biological substance (e.g. antibodies) may be printed locally on the surface of the groove areas 90 or close to the groove areas 90.

Micromagnetic simulation has been performed. Because of the large lateral dimensions (one or more micrometers) of the magnetic biosensor 101 and the ultra-thin free and pinned layers 10 and 30 (typically on the order of 1-10 nanometers) for a typical spin valve type magnetic biosensor, micromagnetic simulation can be carried out using a two dimension (2D) model. The simulation was performed using a well-established 2-D micromagnetic simulation software: the object-oriented micromagnetic framework (OOMMF). With the software, the magnetization behavior of the free layer 10 was simulated under the stray magnetic field 110 from the pinned layer 30 and the dipole magnetic field 112 from the MNPs. In the simulation, an example biosensor 101 with both free and pinned layers 10 and 30 and a groove structure 90 was divided into small cells with the same size (5 nm). Each of the cells of the free and pinned layers 10 and 30 have particular magnetic properties and the simulation gave each of those magnetic cells its own magnetic moment and calcualted the interactions of the magnetic cells with all other cells. Before the MNP 50 bonding, the effective field on the free layer 10 is the sum of the stray magnetic field 110 from all the magnetic cells of pinned layer 30. With the MNP 50 sitting in the groove 90, for simplicity, we assume the center of the MNP 50 is the same level with the center of the free layer 10 as shown in FIG. 2B. The MNP 50 is magnetized by the total stray fields 110 from all the magnetic cells of the free and pinned layers 10 and 30. The dipole magnetic field 112 from the MNP 50 is discretized and incorporated into the OOMMF input as well as the stray field 110 from the pinned layer 30 on the free layer 10. The averaged magnetization orientations of the free layer 10 are computed from the magnetization distribution of the magnetic cells by OOMMF.

Figure 4A:
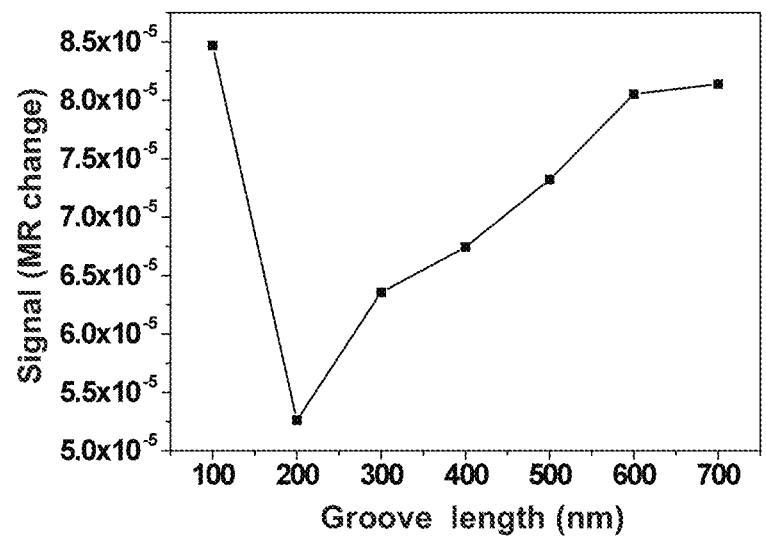
FIGS. 4A and 4B are graphs of the results of a computer simulation performed using the proposed magnetic biosensor.
Figure 4B:
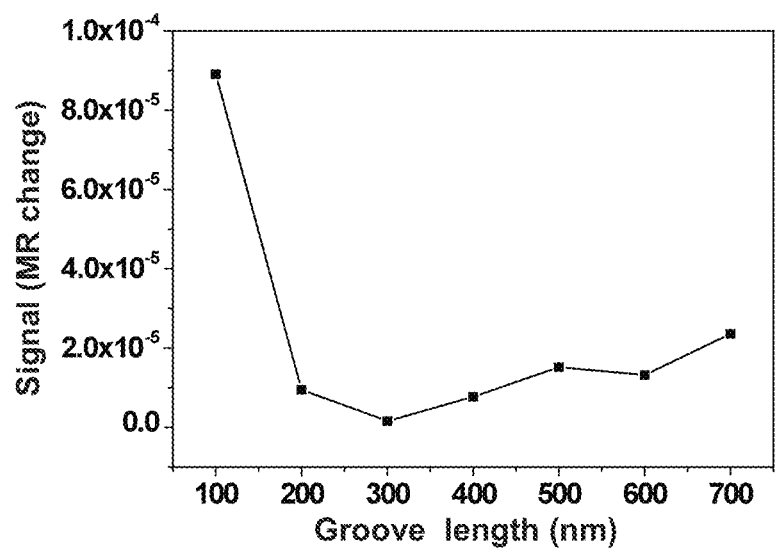

FIGS. 4A and 4B illustrate the results of the simulation. The dimensions of the magnetic biosensor 101 used in the simulation were a length of 3 μm ($L_s$) and a width 0.5 μm wide ($W_s$). The dimensions the groove 90 varied (length $L_g$ and width $W_g$). A commercially available iron oxide MNP 50 was used to explore the maximum sensitivity of the technique described herein. The MNP was simulated to be located at the center of the groove structure 90. The iron oxide magnetic nanoparticle 50 has a saturation magnetization value of 480 emu/cc and size of 8 nm in radius. The signal from the MNP 50 is represented by the change of the magnetoresistive ratio (MR) with and without the presence of the MNP 50. Although specific dimensions for the magnetic biosensor 101 and the groove 90 and a specific MNP 50 were used for the simulation, many different dimensions or MNPs 50 could be used in various embodiments of magnetic biosensors 101.

FIGS. 4A and 4B show the MR change due to the MNP 50 for different groove 90 dimensions. In FIGS. 4A and 4B, the width of the groove 90 is fixed at 100 nm and 200 nm, respectively, while the length of the groove 90 varies from 100 nm to 700 nm. As shown in FIG. 4A, the signal is at the maximum when the groove 90 length is 100 nm (for this particular simulation). The results indicate that the stray fields 110 from the free and pinned layers 10 and 30 acting on the MNP 50 and the interaction between MNP dipole magnetic field 112 and the free layer 110 are strongest at this groove 90 dimension. The signal then decreases rapidly to the minimum with 200 nm groove 90 length and increases as the length increases, suggesting a complex interaction between the stray fields 110, MNP dipole magnetic field 112 and free layer 10.

FIG. 4B, depicting the simulation results with a fixed groove 90 width of 200 nm, shows a maximum signal ($8.9 \times 10^{-5}$) with a 100 nm groove 90 length structure in this simulation. The signal then decreases dramatically with 200 nm groove 90 length and increases slowly with a longer groove 90 structure. In comparison, for a groove structure 90 with a length longer than 200 nm, the simulated biosensor 101 having a 200 nm width shows a more stable signal change than the simulated biosensor 101 with a 100 nm width. This may be due to the fact that there is less magnetic material left on the magnetic biosensor 101 after formation of the groove. As demonstrated by the experimental data, which shows a noise level around $10^{-5}$ MR change using a spin valve biosensor, a sensitivity (around 40 dB) of ten nanoparticles 50 detection can easily be achieved using the detection method described herein.

Figure 5:
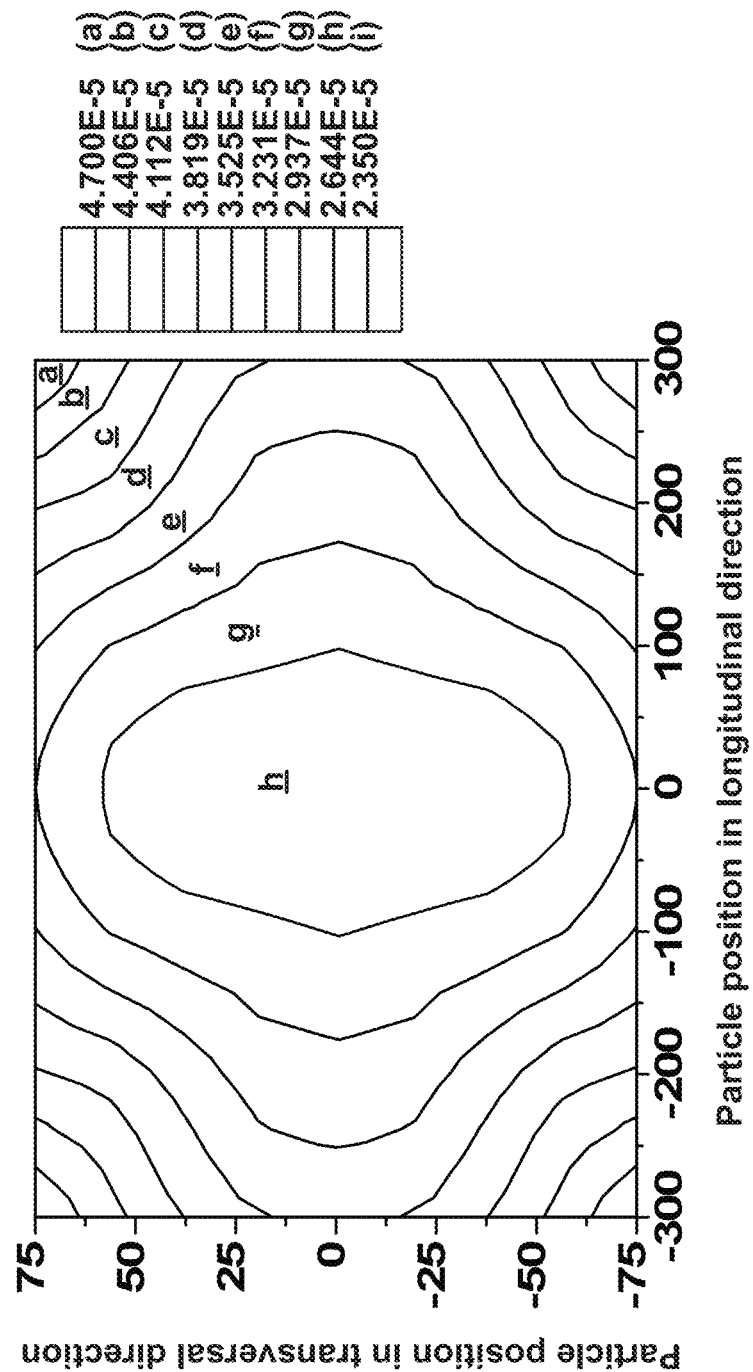
FIG. 5 is a graph of a simulation of the signal produced by the proposed magnetic biosensor with a single magnetic label bound within the groove structure as a function of the magnetic label position.

FIG. 5 is a graph demonstrating an example signal produced by an example magnetic biosensor 101 based on the MNP 50 position inside the groove structure 90. The parameters of the MNP 50 used in this simulation were the same as those used in above-described simulation. The dimensions of the groove were 200 nm in width ($W_g$—transversal direction) and 700 nm in length ($L_g$—longitudinal direction). As shown in FIG. 5, the signal from one iron oxide MNP 50 becomes larger when the MNP 50 locates closer to a corner of the groove structure 90, i.e., a corner of the groove 90 along the surface of the magnetic structure. This may be due to a stronger interaction between the MNP 50 and the free layer 10 because of the larger magnetic stray fields 110 from both free fixed and pinned layers 10 and 30 on the corner of the groove structure 90.

Figure 18:
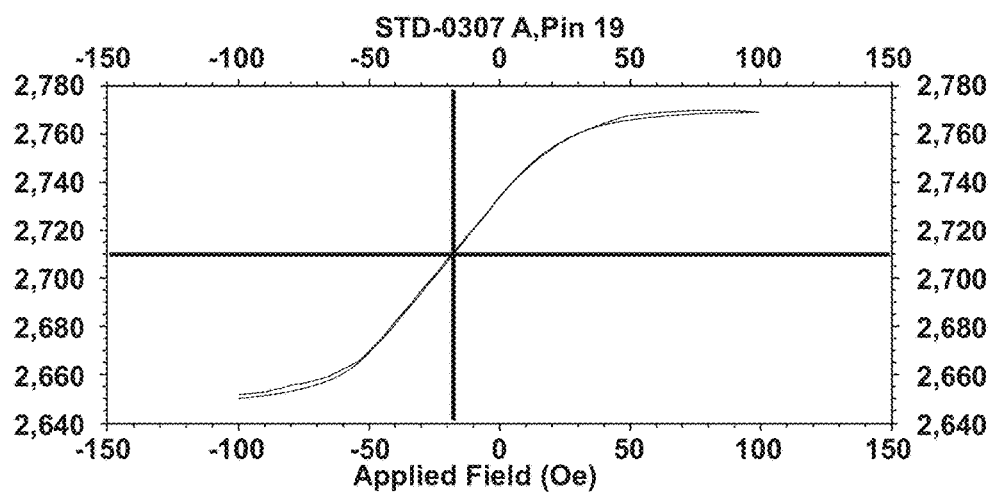
FIG. 18 is a graph of the strength of the stray magnetic field in an example proposed magnetic biosensor as a vagying-strength external magnetic field was applied to the system.
Figure 19:
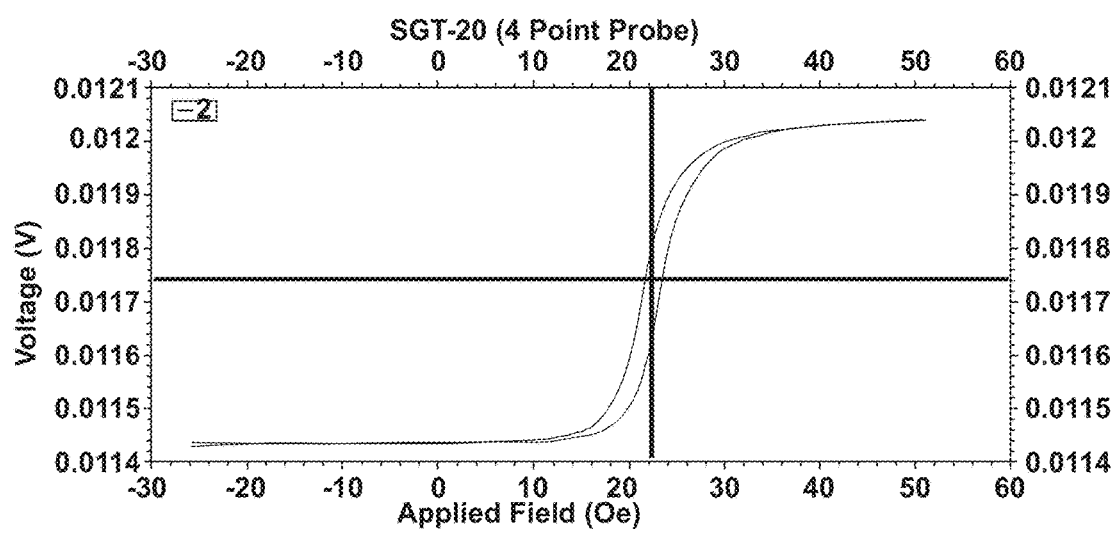
FIG. 19 is a graph of the strength of the stray magnetic field in a conventional magnetic biosensor as a varying-strength external magnetic field was applied to the system.

FIGS. 18 and 19 illustrate the effect of the groove structure 90 on the strength of the stray magnetic field 110 from pinned layer 30. FIG. 19 shows a measurement of the magnetic field hysteresis loop in a magnetic biosensor 100 without a pattern as a varying-strength external magnetic field was applied to the system. The measurements show that the orange peel effect from pinned layer 30 on the free layer 10 is +22 Oe. FIG. 18 shows a measurement of the magnetic field hysteresis loop in an example proposed magnetic biosensor 101 as a vaging-strength external magnetic field was applied to the system. The measurements show that the stray magnetic field 110 overcame the orange peel effect from the pinned layer 30 on the free layer 10 and total stray magnetic field 110 on the free layer was −18 Oe. This means that the total stray magnetic field 110 from the pinned layer 30 in the example magnetic biosensor 101 was −40 Oe, which is strong enough to affect the free layer 10 and magnetize MNPs 50 that are close to the sensor's 101 surface.

Another test was performed to prove the stray magnetic fields 110 from the pinned layer 30 affected the free layer 10. Table 1 below illustrates the results of the test. An example biosensor 101 under a 10 Oe 50 HZ AC external magnetic field was connected with a Wheatstone bridge circuit. A 1V AC carrier tone at 1k Hz was applied through the sensor. The two first harmonic side tones which showed magnetic resistance change under AC field were detected in the freguency spectrum by a National Instrument data ac uisition (DAQ) system. As shown in Table 1, by increasing the offset magnetic field from 0 Oe to 14.4 Oe, the first harmonic side tone varied and the maximum happened when the offset field was 6.6 Oe, which further proves that the free layer 10 was magnetized by the stray magnetic field 110 from pinned layer 30.

TABLE 1

| Offset Field (my/Oe) | First Harmonic (mV 50 Hz) |
| --- | --- |
| 0/0 | 21.996 |
| 1/0.16 | 22.008 |
| 2/0.33 | 22.022 |
| 3/0.5 | 22.037 |
| 4/0.66 | 22.05 |
| 5/0.82 | 22.059 |
| 10/1.6 | 22.117 |
| 20/3.3 | 22.2 |
| 30/4.9 | 22.25 |
| 40/6.6 | 22.26 |
| 50/7.2 | 22.243 |
| 100/14.4 | 21.36 |

Figure 6:
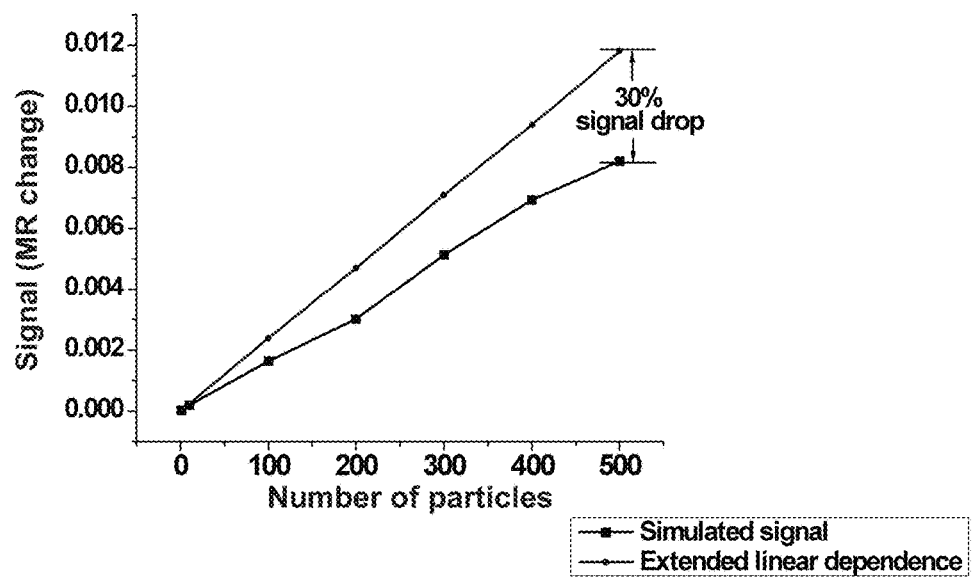
FIG. 6 is a graph of a simulation of the signal produced by the proposed biosensor as a function of the number of magnetic labels bound within the groove structure.

To explore the detection dynamic range in this detection scheme, a simulation of the signal dependence on the number of MNPs 50 in the groove structure 90 was performed. In order to obtain a wide dynamic range, a groove structure 90 of 700 nm length and 200 nm width was chosen due to the large groove structure 90 area to accommodate more MNPs 50. Iron oxide MNPs 50 with same dimension and saturation magnetization as the above simulation were also used in this simulation. The maximum number of MNPs 50 for the simulation was set to 500 so that the distance between each MNP 50 was in a reasonable range for minimizing the interaction between MNPs 50. The MNPs 50 were modeled as being uniformly distributed in the groove structure 90. As shown in FIG. 6, the signal from the magnetic biosensor 101 increased as the number of MNPs bonded within the groove structure 90 increased (black dot curve in FIG. 6). Compared with the extended linear dependence from a single MNP 50 signal (top curve in FIG. 6), the simulated signal from multiple MNPs 50 decreased. However, there was only a 30% signal drop in the 500 MNP 50 case, which indicates that the signal did not reach a plateau before the number of MNPs 50 reached the maximum. Therefore, in an example magnetic biosensor 101 using the disclosed detection scheme, the maximum MNP 50 detection limit may be determined by physical accommodation of MNPs in the groove structures 90.

In this manner, a magnetic biosensing scheme is described that may be utilized without requiring an external magnetic field generator. This may provide many benefits, including, for example, system miniaturization and power consumption control of biosensing systems. In one example, the detection scheme utilizes a groove structure 90 in the biosensor 101, and employs the stray fields 110 from free and pinned layers 10 and 30 of the magnetic biosensor 101 for MNP magnetization.

As described above, micromagnetic simulations were carried out for an example magnetic biosensor 101 using the disclosed detection scheme. Signals from different groove structures 90 were calculated. The results showed a good signal level and an example maximum $8.9 \times 10^{-5}$ MR change from one 8 nm radius iron oxide MNP 50 locating on the center of the groove structure 90. The signal dependence on the MNP 50 position in the groove structure 90 was investigated. The results suggested an increased signal level on the corner of the groove structure 90. The dynamic detection range of example magnetic biosensors 101 using this detection scheme was explored by simulating signal from multiple MNPs 50 in the groove structure 90. The results demonstrated that the signal increases as more MNPs 50 are bonded in the groove structure 90. Moreover, the simulation showed that uniformly distributed 500 MNPs 50 do not saturate the sensor signal. As such, the detection scheme may be limited only by the physical accommodation of MNPs 50 in the groove structure 90.

Figure 9B:
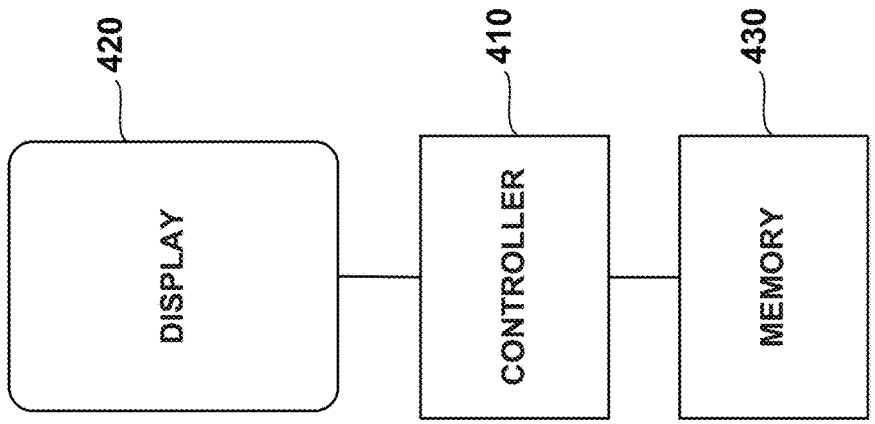
FIGS. 9A and 9B illustrate an example handheld device that utilizes the proposed magnetic biosensing detection scheme.
Figure 9A:
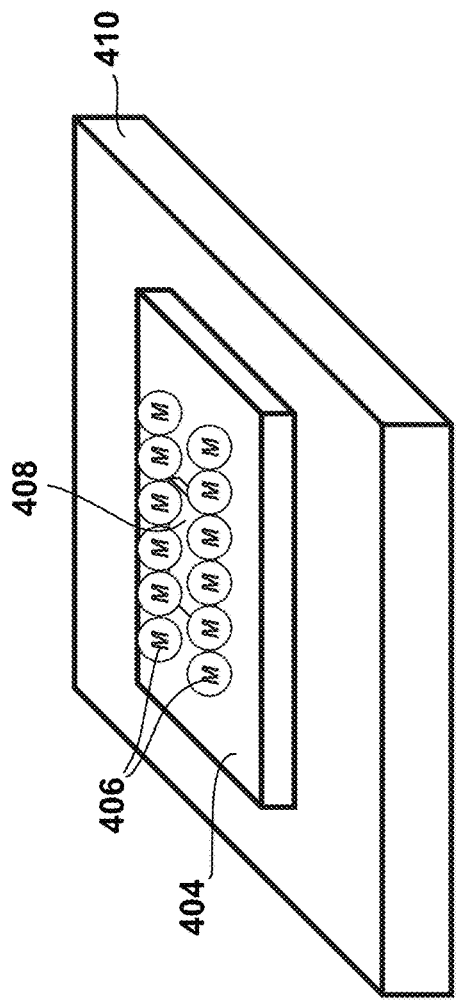

FIGS. 9A and 9B illustrate an example handheld device that utilizes the detection scheme described herein. The handheld device may possibly be the size of a cell phone or smaller and comprises a magnetic sensing chip 404 (e.g. a magnetic biosensor), a controller 410 to receive and process the electrical signal from the sensing chip, a display screen 420 to provide a user interface and to present any sensed output to a user. Like the before-described magnetic biosensor, the magnetic sensing chip 404 may have a groove structure 408 and may have components that allow MNPs 406 to bind to the sensing chip 404. The controller 410 may be a field programmable gate array (FPGA), a general purpose processor, a digital signal processor or other suitable electronic component. The handheld device may include a computer-readable medium 430 to store software instructions (e.g., a memory) for execution by the processor to perform the sensing techniques described herein. In some embodiments the sensing chip 404 is incorporated into an electronic component that may be coupled, mounted on, tethered or otherwise connected to a handheld device.

FIGS. 10A and 10B illustrate two example configurations of a field-free magnetic sensor. FIG. 10A shows a strip-type magnetic biosensor 400a in which a grooved pattern is formed to include a plurality of parallel linear grooves surrounded by the magnetic sensing 404a. The MNPs 406a may collect in the grooves, on the sensing strips, or both. Other patterns may be formed, such as a pattern of curved grooves, a pattern of sawtooth grooves, or combinations thereof. FIG. 10B shows a second example in which the magnetic sensor 400b has a magnetic sensing substrate 404b that is patterned with notches 408b. Each of the notches 404b forms a single, short groove into the surface of the magnetic sensing substrate 404b. MNPs 50 406b illustrate how they fit into the notches 404b.

Figure 17:
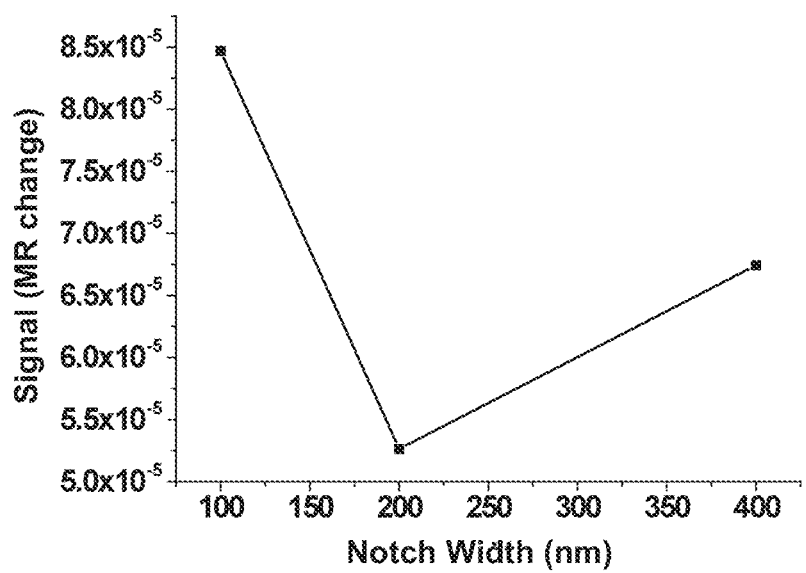
FIG. 17 is a graph of a simulation of the signal produced by the proposed magnetic biosensor with a single magnetic label bound within a notch structure where the notch structure has a fixed length of 100 nm and a vaging width between 100 and 400nm.

FIG. 17 is a graph of a simulation of signal produced by a proposed magnetic biosensing device with a notch structure. The simulation used a notch length of 100 nm and varied the notch width between 100 and 400 m. The graph illustrates a maximum signal when the notch width was 100 nm and a minimum when the notch width was 200 nm. The graph also illustrates a slow increase in signal as the notch width was increased beyond 200 nm.

Figure 11:
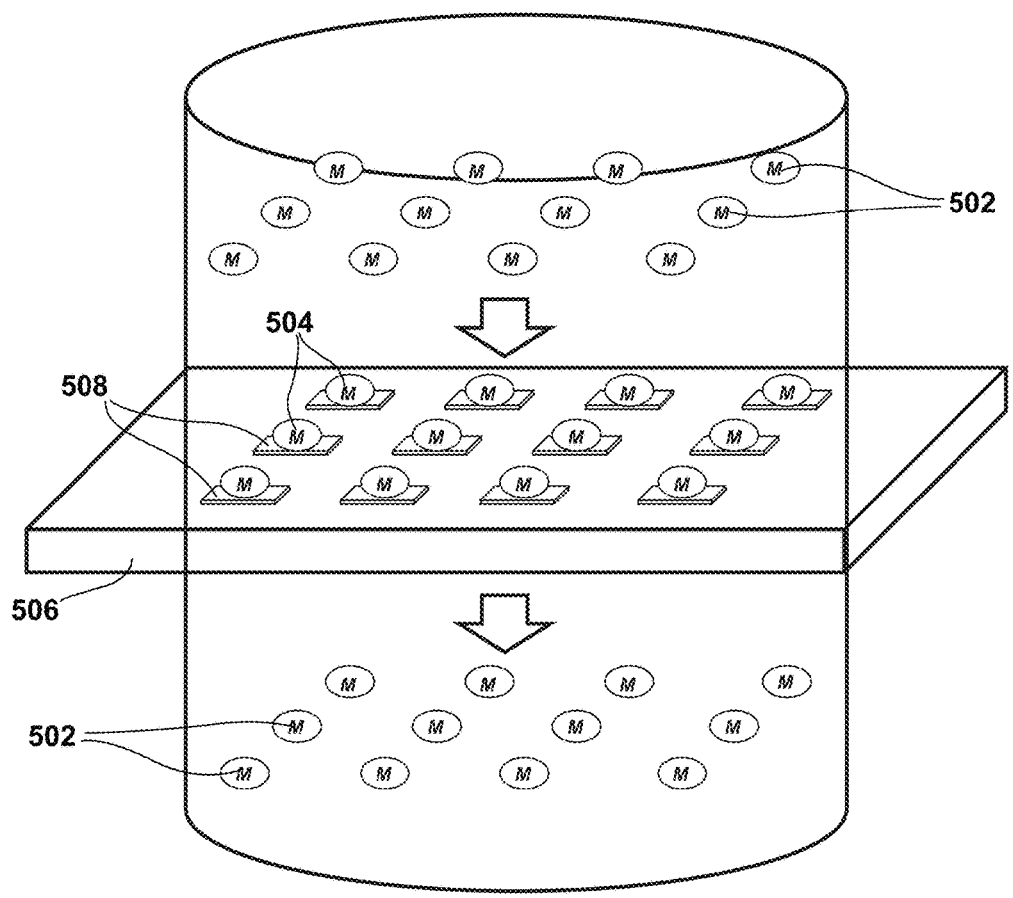
FIG. 11 illustrates an example flow of direction of unbound magnetic labels through an example proposed magnetic biosensing chip 506 having a grooved pattern formed from a plurality of notches.

FIG. 11 illustrates example flow of direction of unbound magnetic labels (nanoparticles, microbeads) 502 through an example sensing chip 506 having a grooved pattern formed from a plurality of notches 508. Some of the unbound magnetic labels 502 bind to the sensing chip 506 and become bound magnetic labels 504.

Figure 12:
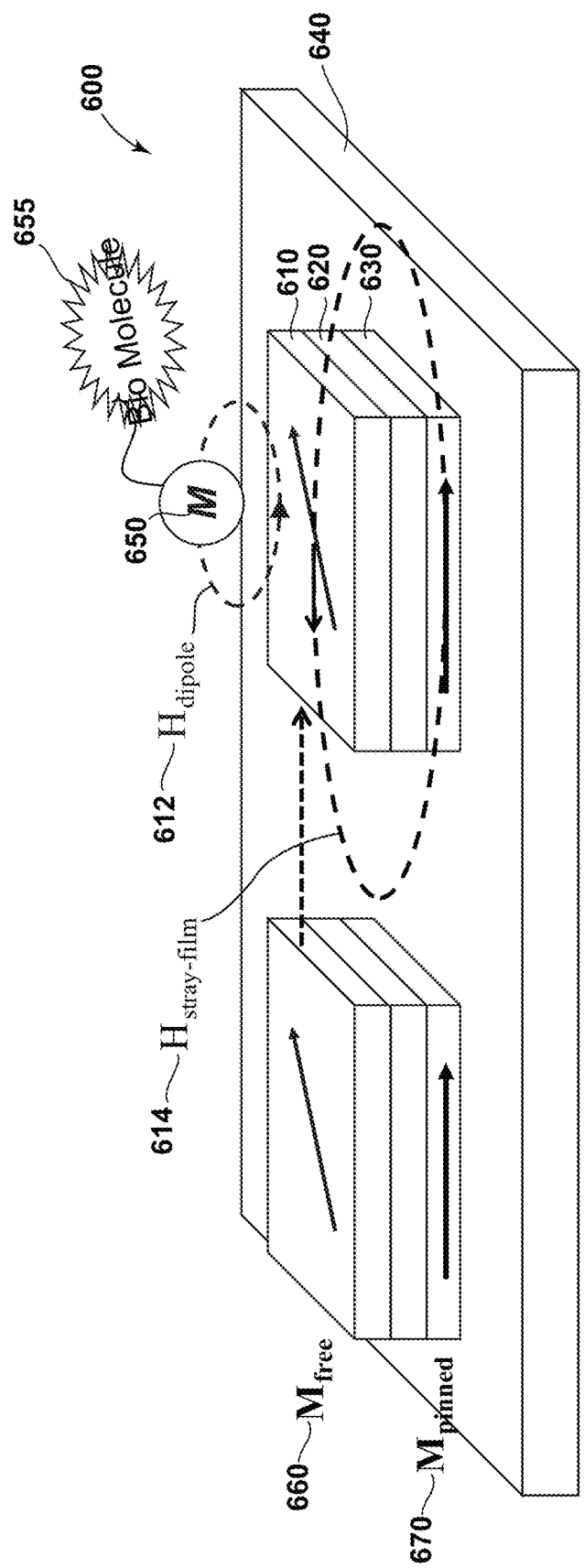
FIG. 12 illustrates an example proposed magnetic biosensor configured so that the magnetic labels only bind to the surface of the biosensor.

FIG. 12 illustrates further details of the field free biosensing detection scheme. Magnetic biosensor 600 is similar to the biosensor 101 depicted in FIGS. 2A and 2B. Biosensor 600 includes a free layer 610, a spacer layer 620, and a pinned layer 630. The biosensor 600 may also include a substrate layer 640. Similarly to biosensor 101, the free and pinned layers 610 and 630 are magnetized, as denoted by the arrows and by the reference numbers 660 and 670. As shown, the magnetic biosensor 600 may be configured so that the MNPs 650 only adhere to the surface of the biosensor 600. The MNP 650 is also bonded to a biological molecule of interest 655. In biosensor 600, the stray magnetic fields 614 from the free and pinned layers 610 and 630 magnetize the MNP 650. Once magnetized, the MNP 650 produces a dipole magnetic field 612. The dipole magnetic field 612 and the stray magnetic fields 110 interact with the magnetic field 660 in the free layer 610. The interaction produces a signal that may be read and interpreted by an electronic system (not depicted). Other embodiments of biosensor 600 may use an externally applied magnetic field (not depicted) to enhance the signal of the biosensor 600.

Figure 13:
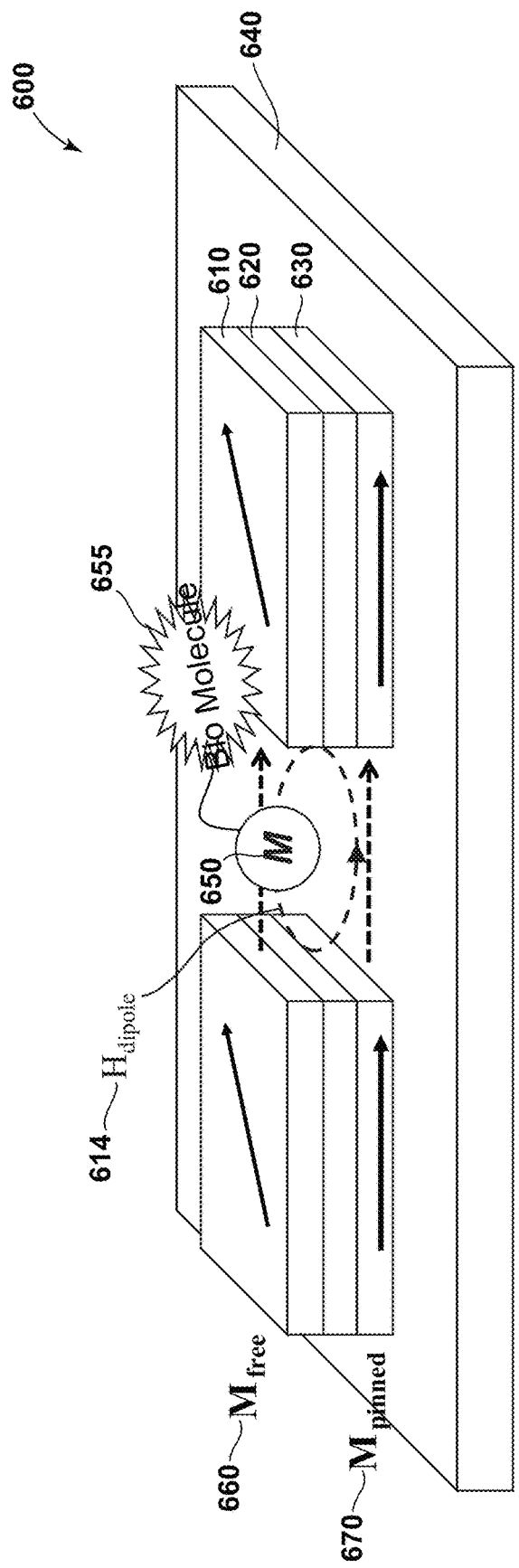
FIG. 13 illustrates an example proposed magnetic biosensor configured so that the magnetic labels only bind in the groove of the biosensor.

FIG. 13 illustrates a further embodiment of biosensor 600. As shown, the magnetic biosensor 600 may be configured so that the MNPs 650 only adhere to within the groove 90 of the biosensor 600. The MNP 650 is also bonded to a biological molecule of interest 655. In biosensor 600, the stray magnetic fields 614 from the free and pinned layers 610 and 630 magnetize the MNP 650. Once magnetized, the MNP 650 produces a dipole magnetic field 612. The dipole magnetic field 612 and the stray magnetic fields 110 interact with the magnetic field 660 in the free layer 610. The interaction produces a signal that may be read and interpreted by an electronic system (not depicted). Other embodiments of biosensor 600 may use an externally applied magnetic field (not depicted) to enhance the signal of the biosensor 600.

Figure 14:
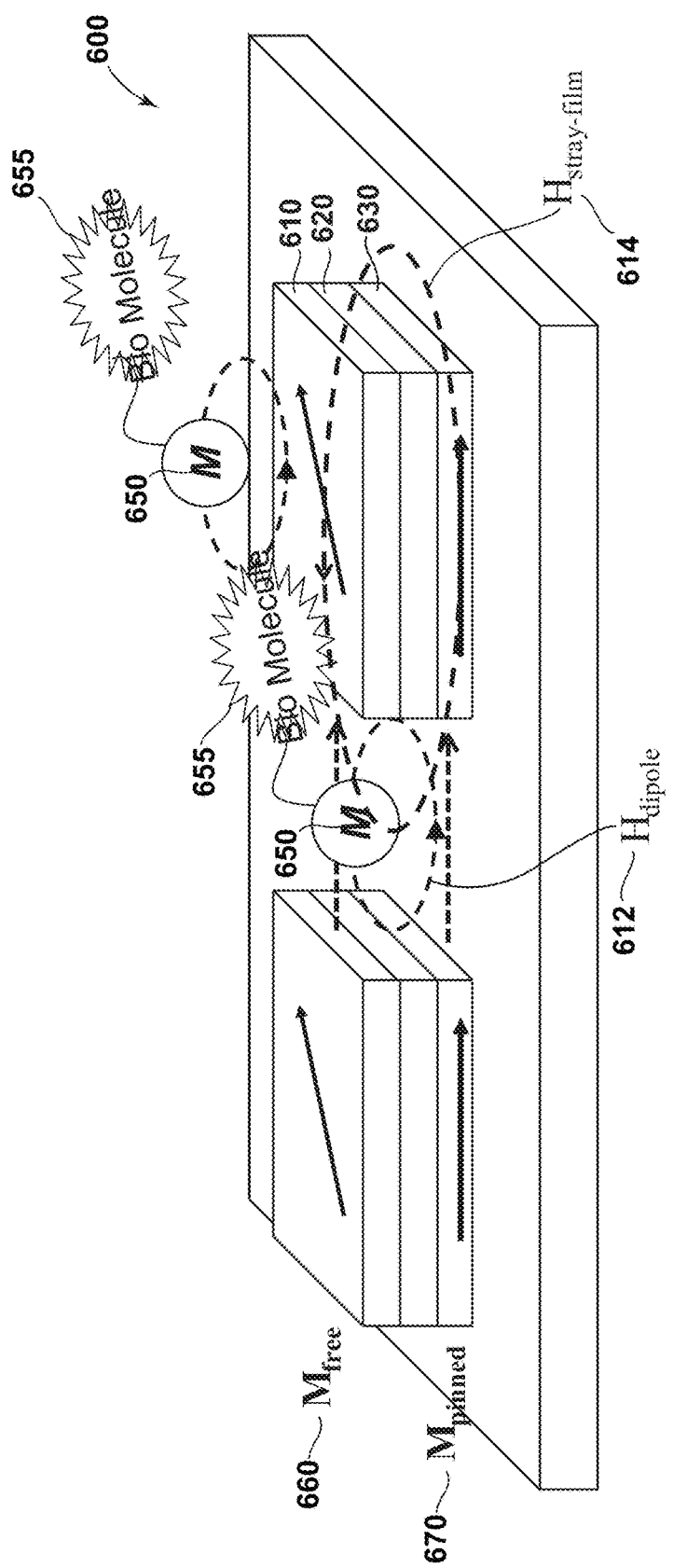
FIG. 14 illustrates an example proposed magnetic biosensor configured so that the magnetic labels can bind both to the surface of the biosensor and in the groove of the biosensor.

FIG. 14 illustrates a further embodiment of biosensor 600. As shown, the magnetic biosensor 600 may be configured so that the MNPs 650 adhere both within the groove 90 of the biosensor 600 and on the surface of the biosensor 600, above the groove. The MNPs 650 are also bonded to a biological molecule of interest 655. In biosensor 600, the stray magnetic fields 614 from the free and pinned layers 610 and 630 magnetize the MNPs 650. Once magnetized, the MNPs 65O produces dipole magnetic fields 612. The dipole magnetic fields 612 and the stray magnetic fields 110 interact with the magnetic field 660 in the free layer 610. The interaction produces a signal that may be read and interpreted by an electronic system (not depicted). Other embodiments of biosensor 600 may use an externally applied magnetic field (not depicted) to enhance the signal of the biosensor 600.

Figure 15:
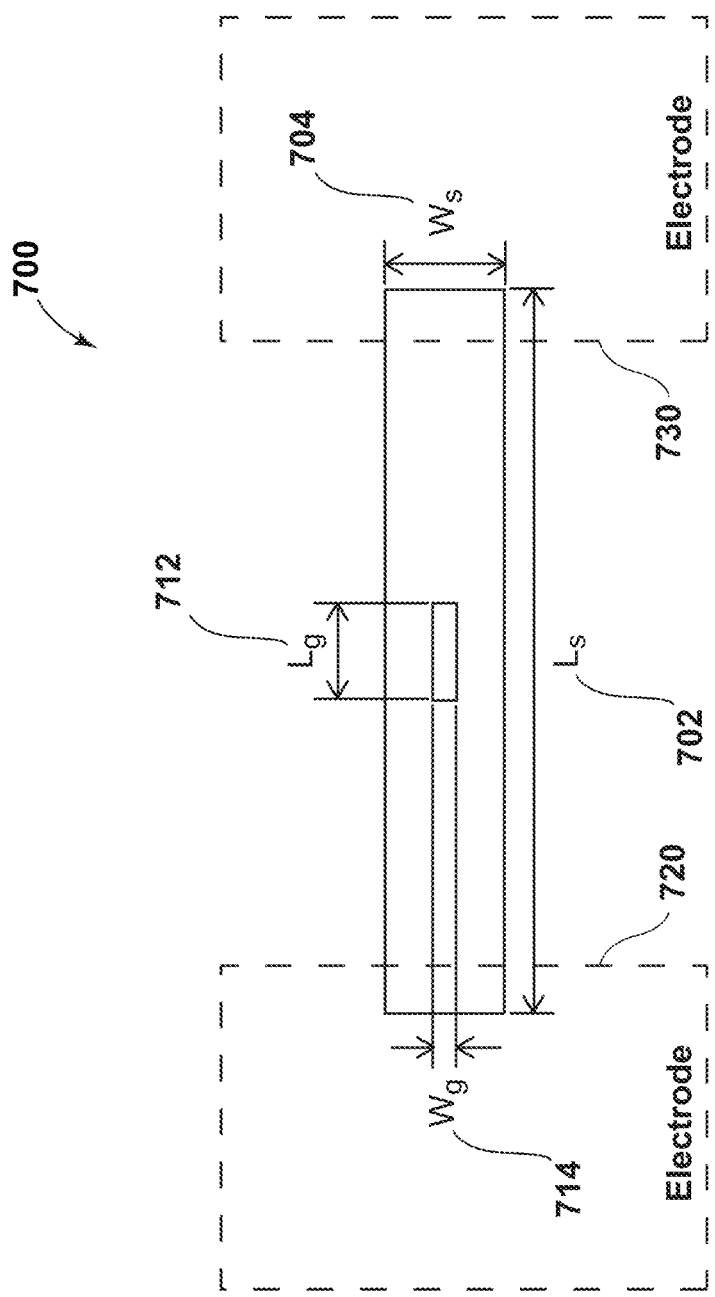
FIG. 15 illustrates an example of the proposed magnetic biosensing chip connected to two electrodes.
Figure 16:
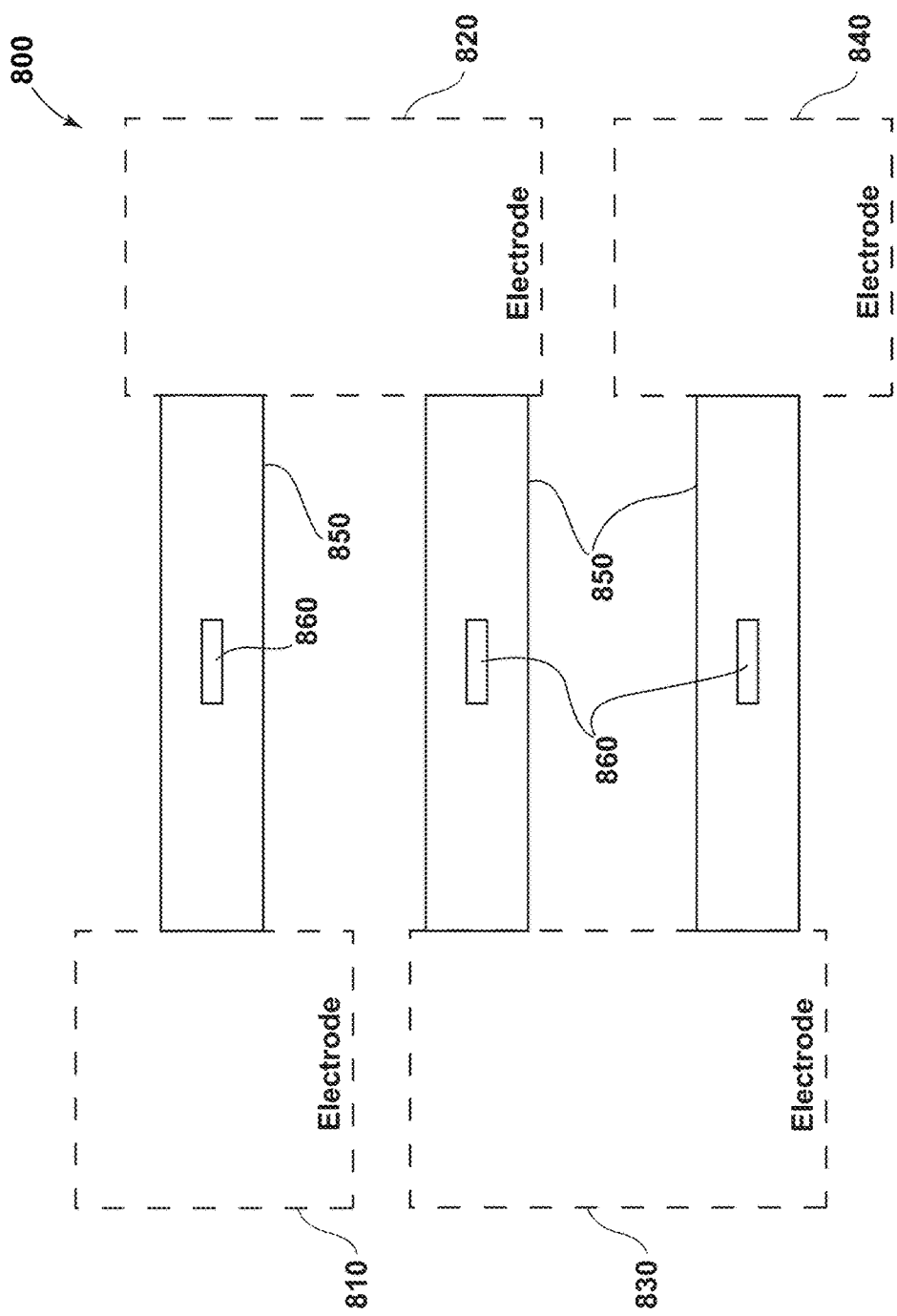
FIG. 16 illustrates an example of multiple proposed magnetic biosensing chips connected to multiple electrodes.

FIGS. 15 and 16 are top-down views showing two examples of electric sensing chips utilizing the biosensing devices described herein. The chips 700 and 800 are formed with a plurality of electrodes electrically connected to the magnetic biosensor having a grooved pattern. FIG. 15 depicts sensor 700. Sensor 700 includes a first electrode 720 connected to a second electrode 730 by a biosensing device. The biosensing device has a width 704, $W_s$, and a length 702 $L_s$. The biosensing device also has a groove structure patterned on its surface. The groove structure may be any of the structure described in this application and may generally have a width 714, $W_g$ and a length 712, $W_g$.

FIG. 16 depicts an alternate configuration of an electric sensing chip 800. Chip 800 includes a first electrode 810 connected to a second electrode 820. The second electrode is also connected to a third electrode 830. The third electrode is also connected to a fourth electrode 840. Connected between the first and second electrodes, the second and third electrodes, and the third and fourth electrodes are magnetic biosensors 850. Each of the biosensors includes a groove structure 860. Although only two specific examples of electrode configurations are depicted, many other well-known combinations could be used as well. In the electrical chips 700 and 800, the electrodes provide electrical connections for reading the electrical signal produced by magnetic biosensors.

An experiment was also performed with a fabricated GMR strip-type sensor. Groove structures were patterned directly on each sensor stripe: using E-beam lithography. Two types of structures were tried: 1. 200×200 nm groove structure and 500 nm vertical distance; 2. 100×100 nm groove structure and 500 nm vertical distance. FIG. 20 shows the layout and dark field microscope images. In the real-time MNP binding test, the sensor surface was pre-wet with DI water to stabilize the temperature. 30 μL DI water was dropped on the sensor to see if side tone signals changed at around the $25^{th}$ loop. (One loop lasts one minute). Then 30 μL 30 nm MNP was loaded at around the $50^{th}$ loop. FIGS. 21 and 22 show the real-time signals of both 200 nm and 100 nm grooves.

Various embodiments of the invention have been described. These and other embodiments are within the scope of the following claims.

The invention claimed is:
1. A biosensor comprising:
   a magnetic structure comprising a surface and a spin valve structure having a free layer and a pinned layer; and
   a groove formed within the surface to biologically bond magnetic labels to a biological substance within or above the groove;
   wherein the groove is positioned within the magnetic structure so that stray magnetic fields from both the free layer and the pinned layer pass through the groove for magnetization of the magnetic labels without the presence of an external applied magnetic field through the groove, and wherein the biosensor does not comprise a field-generating current line.

2. The biosensor of claim 1, wherein the magnetic labels comprise magnetic nanoparticles (MNPs) having a diameter of less than approximately 100 nanometers.

3. The biosensor of claim 1, wherein the magnetic labels comprise magnetic microbeads having a diameter of between approximately 1 and 2 microns.

4. The biosensor of claim 1, wherein the groove is formed to extend through the free layer and at least a portion of the pinned layer.

5. The biosensor of claim 1, wherein the free layer ranges from 1 to 10 nm in thickness and the pinned layer ranges from 10 to 50 nm in thickness.

6. The biosensor of claim 1, wherein the groove is approximately 5 to 100 nanometers in depth.

7. The biosensor of claim 1, wherein the biosensor comprises one of a giant magnetoresistance (GMR) sensing device having the spin valve structure, a magnetic tunnel junction (MTJ) sensing device having the spin valve structure, a giant magnetoimpedance (GMI) sensing device having the spin valve structure or a Hall sensing device having a soft magnetic layer underneath a Hall sensing layer, the soft magnetic layer responding to a sensing current and generating the magnetic field.

8. The biosensor of claim 1, wherein the groove has a depth sufficient to contain the biological substance and biologically bond the magnetic label onto the biological substance within the groove.

9. The biosensor of claim 1, wherein the groove is approximately 2 to 3 times a width of the magnetic labels.

10. The biosensor of claim 1, further comprising at least one electrode to output an electrical signal representative of the bonding of the magnetic labels to the magnetic structure.

11. The biosensor of claim 1, wherein the magnetic structure has a lateral dimension of at least one micrometer and the magnetic structure has a thickness of less than 500 nanometers.

12. The biosensor of claim 11, wherein the magnetic structure has a thickness of less than 100 nanometers.

13. The biosensor of claim 1, wherein the magnetic structure is less than approximately 3 µm long and is approximately 0.5 µm wide.

14. The biosensor of claim 1, wherein the biosensor outputs a signal indicative of the detection of as few as ten magnetic labels bonded within the groove.

15. The biosensor of claim 1, wherein the groove conforms to one of a linear, curved, sinusoidal, or sawtooth profile.

16. The biosensor of claim 1, wherein the groove comprises one or more notches formed in the surface of the biosensor.

17. A method of manufacturing a magnetic biosensor chip, comprising:
forming a multi-layered magnetic structure on a substrate, the magnetic structure formed to have a grooved surface to biologically bond magnetic labels within a groove surface and a spin valve structure having a free layer and a pinned layer, wherein the magnetic structure is formed so that stray magnetic fields from both the free layer and the pinned layer pass through the groove for magnetization of the magnetic labels without the presence of an external applied magnetic field through the groove, and wherein the magnetic biosensor chip does not comprise a field-generating current line.

18. The method of claim 17, wherein the magnetic labels comprise magnetic nanoparticles (MNPs) having a diameter of less than approximately 100 nanometers.

19. The method of claim 17, wherein the magnetic labels comprise magnetic microbeads having a diameter of between approximately 1 and 2 microns.

20. The method of claim 17, wherein the groove is formed to extend through the free layer and at least a portion of the pinned layer.

21. The method of claim 17, wherein the free layer is formed to have thickness ranging from 1 to 10 nm in thickness and wherein the pinned layer is formed to have a thickness ranging from 10 to 50 nm in thickness.

22. The method of claim 17, wherein the groove is formed to have a thickness approximately 10 to 100 nanometers in depth.

23. The method of claim 17, wherein the biosensor comprises one of a giant magnetoresistance (GMR) sensing device having the spin valve structure, a magnetic tunnel junction (MTJ) sensing device having the spin valve structure, a giant magnetoimpedance (GMI) sensing device having the spin valve structure or a Hall sensing device having the spin valve structure.

24. The method of claim 17, wherein the groove is formed to have a depth sufficient to contain a biological substance and biologically bond the magnetic label onto the biological substance and within the groove.

25. The method of claim 17, wherein the groove is formed to have a width approximately 2 to 3 times a width of the magnetic labels.

26. The method of claim 17, further comprising forming at least one electrode within the magnetic biosensor chip to include to output an electrical signal representative of the bonding of the magnetic labels to the magnetic structure.

27. The method of claim 17, further comprising forming the magnetic structure to have a lateral dimension of at least one micrometer and a thickness of less than 500 nanometers.

28. The method of claim 17, further comprising forming the magnetic structure to have a thickness of less than 100 nanometers.

29. The method of claim 17, further comprising forming the magnetic structure to be less than approximately 3 µm long and approximately 0.5 µm wide.

30. A hand-held device comprising:
a sensing chip comprising a magnetic structure having a groove formed within a surface of the biosensor to biologically bond magnetic labels to a biological substance within the groove surface and a spin valve structure having a free layer and a pinned layer, wherein the groove is positioned within the magnetic structure so that stray magnetic fields from both the free layer and the pinned layer pass through the groove for magnetization of the magnetic without the presence of an external applied magnetic field through the groove, and wherein the hand-held device does not comprise a field-generating current line;
a controller to receive and process an electrical signal from the sensing chip, wherein the electrical signal provides an indication of the number of magnetic labels biologically bonded to the sensing chip; and
a display screen coupled to the controller to provide output indicative of the number of magnetic labels to a user.

31. The device of claim 30, wherein the magnetic labels comprise magnetic nanoparticles (MNPs) having a diameter of less than approximately 100 nanometers.

32. The device of claim 30, wherein the magnetic labels comprise magnetic microbeads having a diameter of between approximately 1 and 2 microns.

* * * * *